United States Patent
Zhao et al.

(10) Patent No.: US 11,359,200 B2
(45) Date of Patent: Jun. 14, 2022

(54) CANCER TREATMENT BY MALAT1 INHIBITION

(71) Applicant: THE CLEVELAND CLINIC FOUNDATION, Cleveland, OH (US)

(72) Inventors: JianJun Zhao, Cleveland, OH (US); Yi Hu, Cleveland, OH (US); Jing Fang, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 167 days.

(21) Appl. No.: 16/497,566

(22) PCT Filed: Apr. 9, 2018

(86) PCT No.: PCT/US2018/026685
§ 371 (c)(1),
(2) Date: Sep. 25, 2019

(87) PCT Pub. No.: WO2018/191153
PCT Pub. Date: Oct. 18, 2018

(65) Prior Publication Data
US 2021/0102212 A1    Apr. 8, 2021

Related U.S. Application Data

(60) Provisional application No. 62/483,396, filed on Apr. 9, 2017.

(51) Int. Cl.
| | |
|---|---|
| *C07H 21/04* | (2006.01) |
| *A61K 48/00* | (2006.01) |
| *C12N 15/113* | (2010.01) |
| *A61K 47/52* | (2017.01) |
| *A61P 35/00* | (2006.01) |
| *A61K 45/06* | (2006.01) |

(52) U.S. Cl.
CPC .......... *C12N 15/1135* (2013.01); *A61K 45/06* (2013.01); *A61K 47/52* (2017.08); *A61P 35/00* (2018.01); *C12N 15/113* (2013.01); *C12N 2310/11* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 7,772,389 B2 * | 8/2010 | Tuschl | C12N 15/113 536/24.5 |
| 2013/0225659 A1* | 8/2013 | Bennett | A61P 21/00 514/44 A |

FOREIGN PATENT DOCUMENTS

| | | | | |
|---|---|---|---|---|
| WO | WO 2011/006121 A2 * | 1/2011 | ........... | C12N 15/113 |
| WO | WO 2012/012467 A2 * | 1/2012 | ........... | C12N 15/113 |
| WO | WO 2013/096837 A1 * | 6/2013 | ........... | C12N 15/113 |
| WO | WO 2016/138017 A1 * | 9/2016 | ........... | C12N 15/113 |

OTHER PUBLICATIONS

Gutschner et al. (Cancer Res, 73(3), 2013, 1180-1189).*
Yoshimoto et al. (Biochimica et Biophysica Acta, 1859, 2016, 192-199).*
Malek et al. (Genes, 2016, 7, 84, 1-13).*
Yuan et al. (Biochemical and Biophysical Research Communications, 478, 2016, 1067-1073).*

* cited by examiner

*Primary Examiner* — Amy H Bowman
(74) *Attorney, Agent, or Firm* — Tarolli, Sundheim, Covell & Tummino LLP

(57) ABSTRACT

Compositions and methods for treating cancer in a subject in need thereof are described that includes administering a therapeutically effective amount of an oligonucleotide that specifically hybridizes to MALAT1.

14 Claims, 16 Drawing Sheets
Specification includes a Sequence Listing.

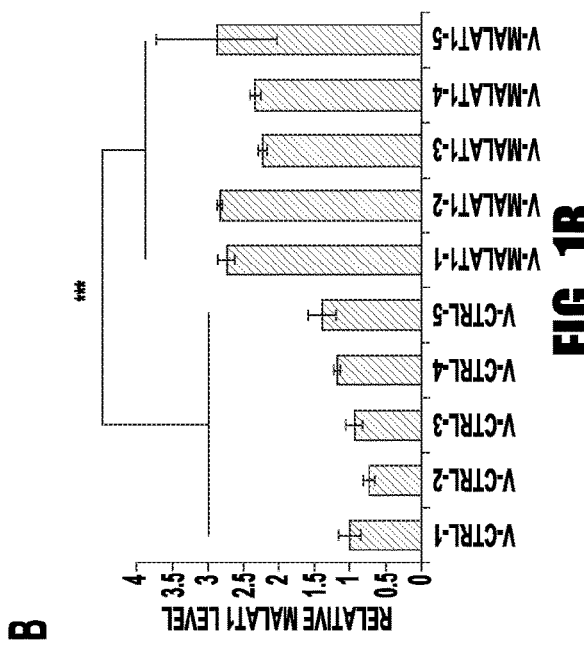
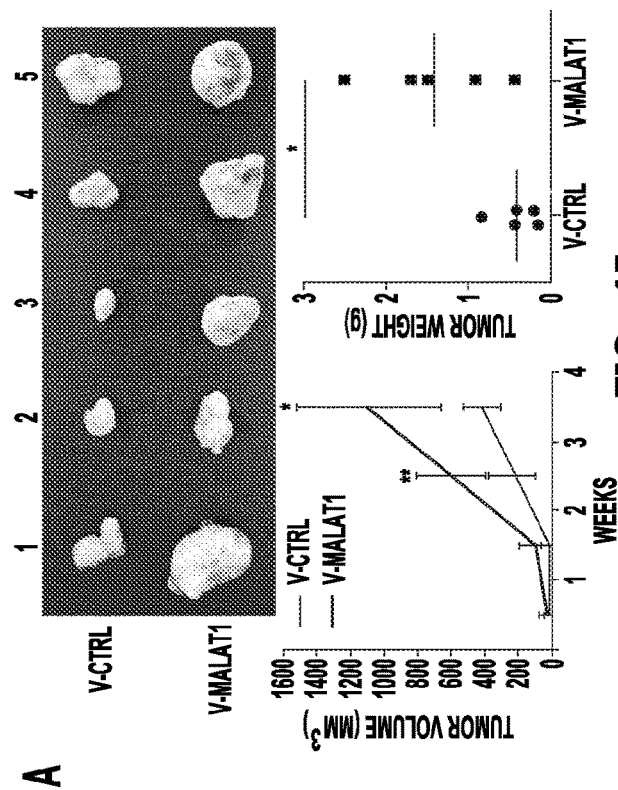
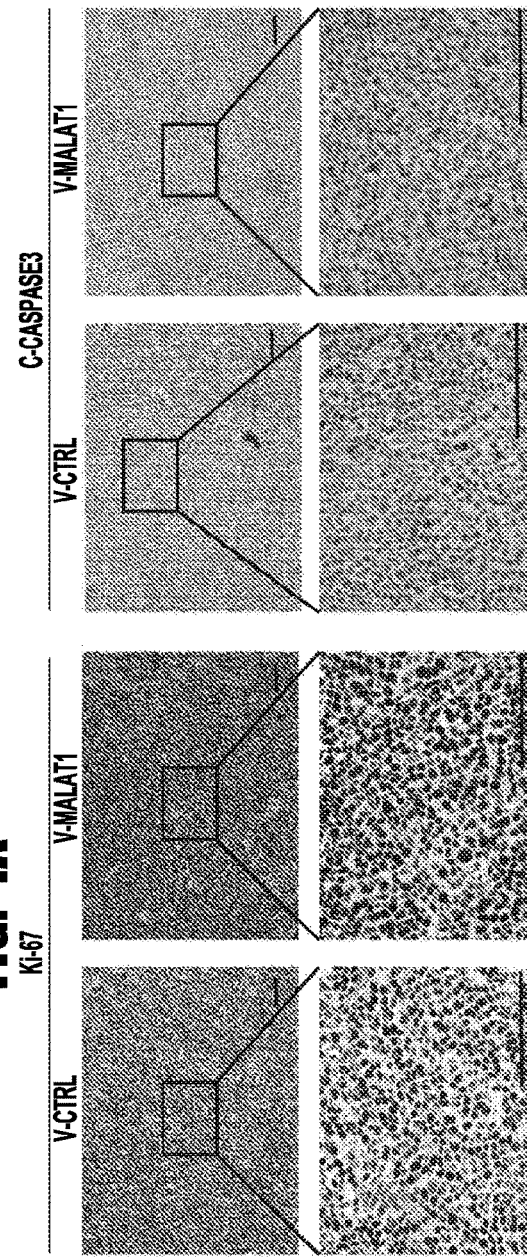
FIG. 1A
FIG. 1B
FIG. 1C

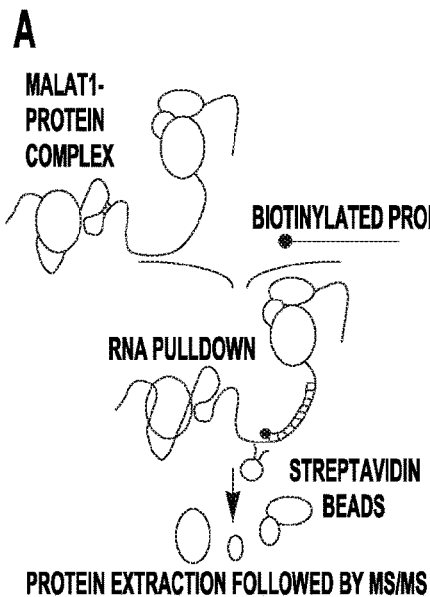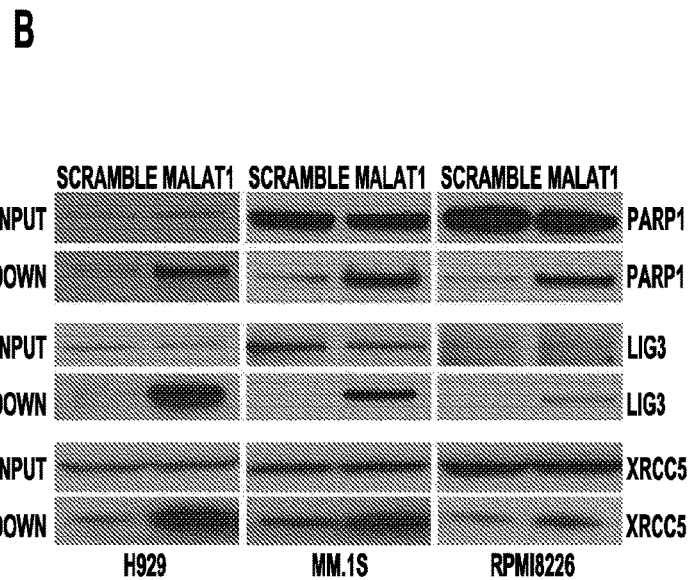
FIG. 2A
FIG. 2B
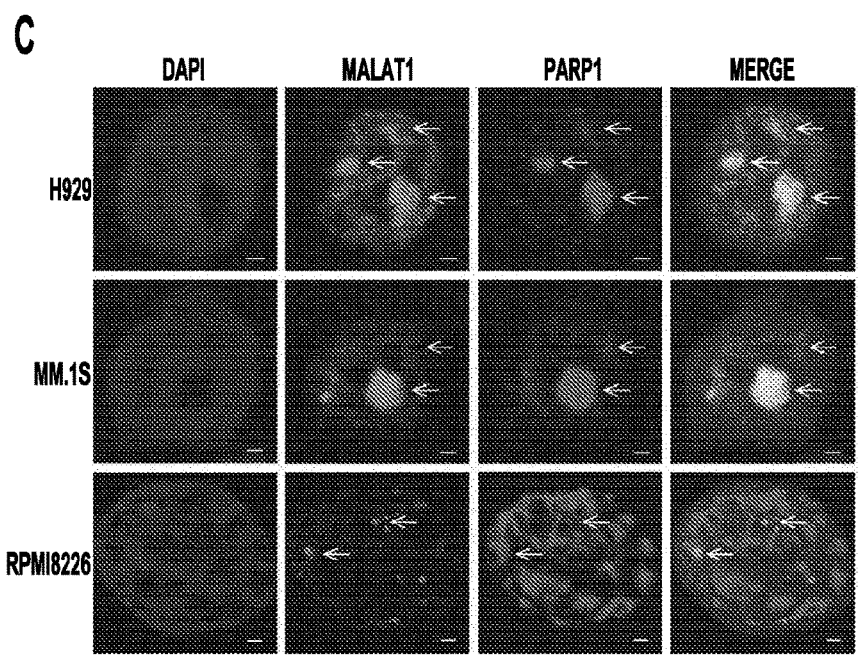
FIG. 2C

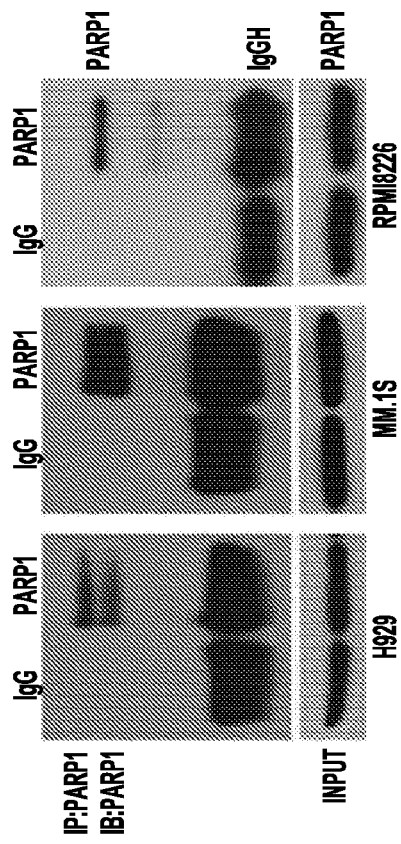
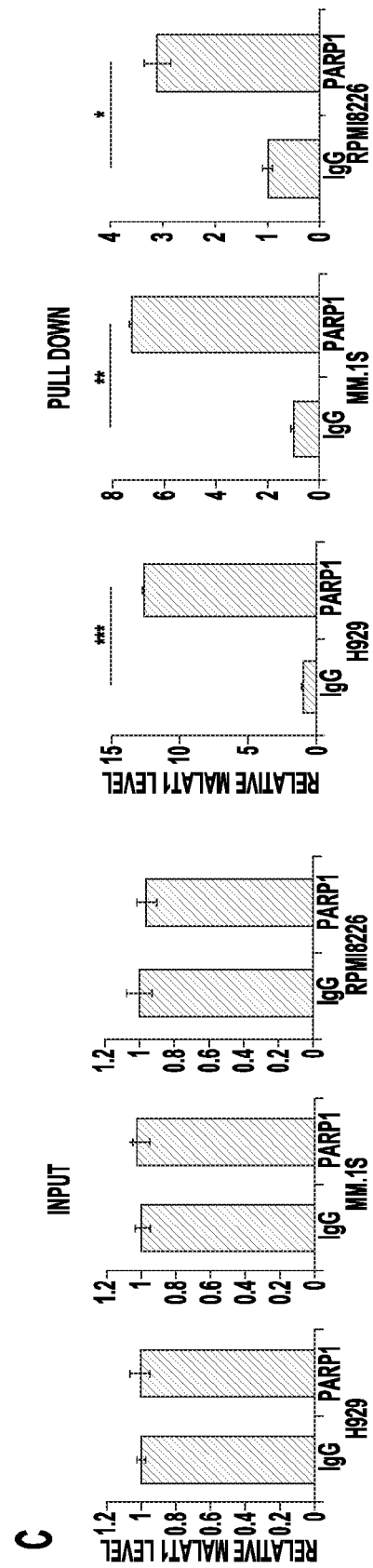
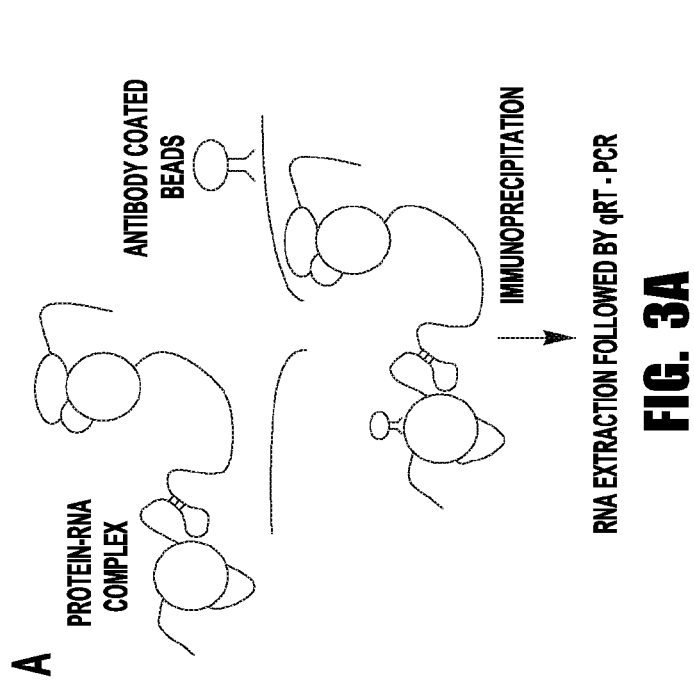
FIG. 3A
FIG. 3B
FIG. 3C

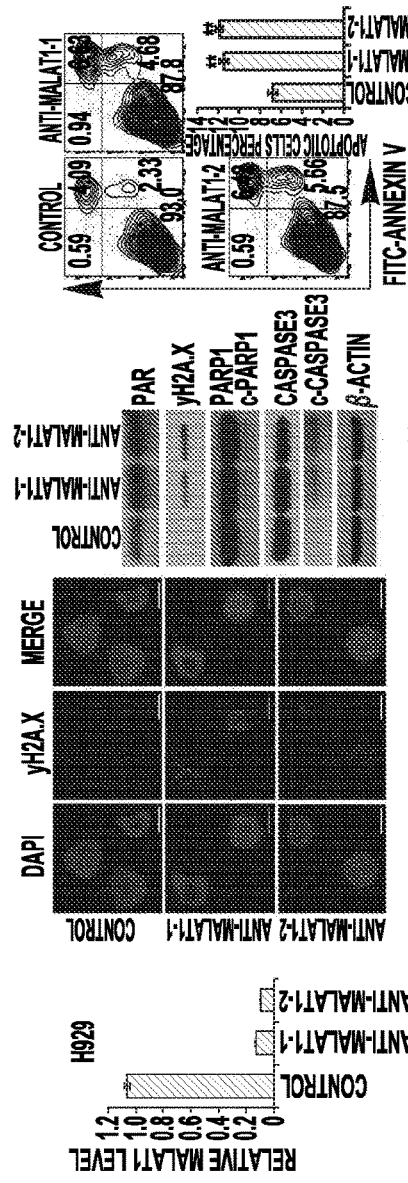
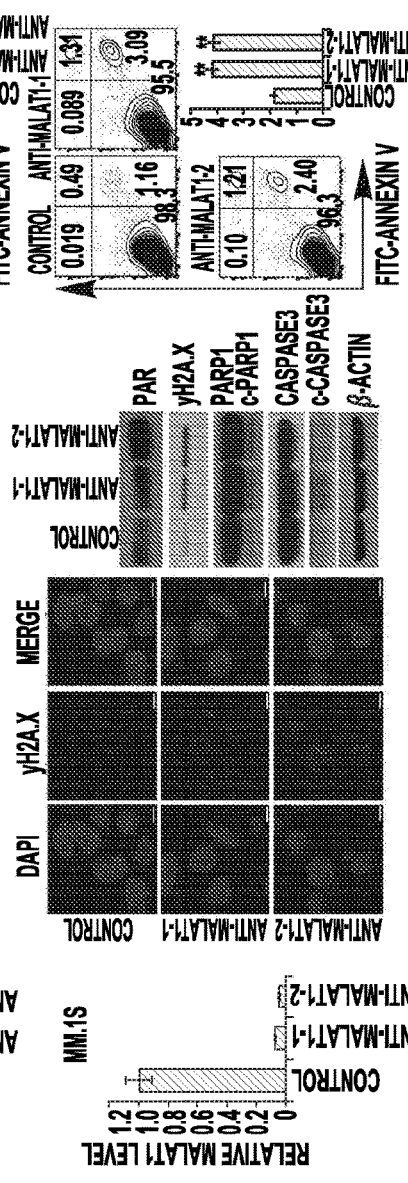
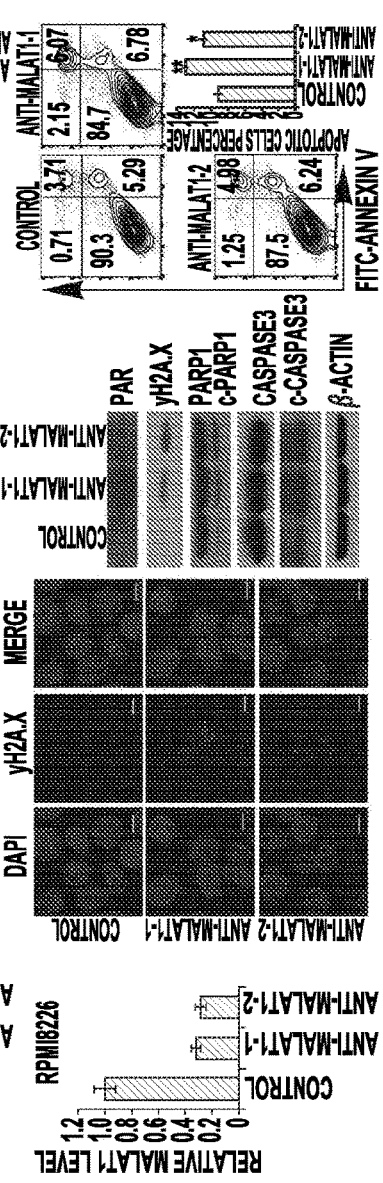
FIG. 4A
FIG. 4B
FIG. 4C

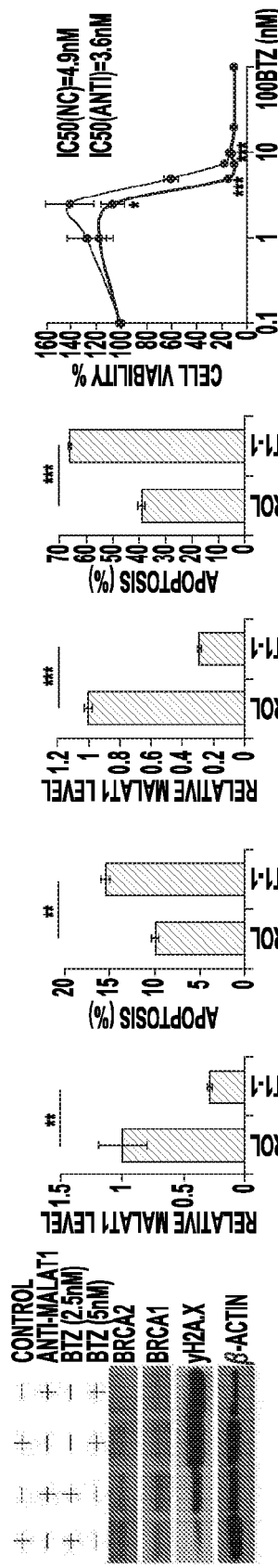
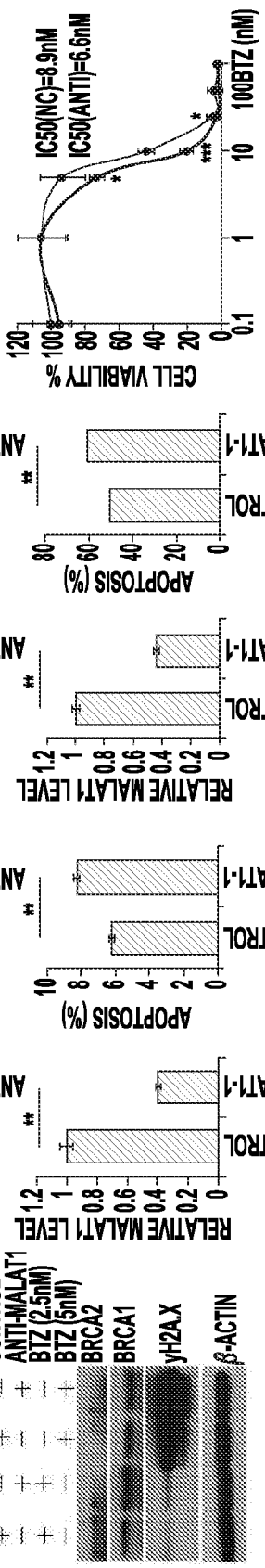
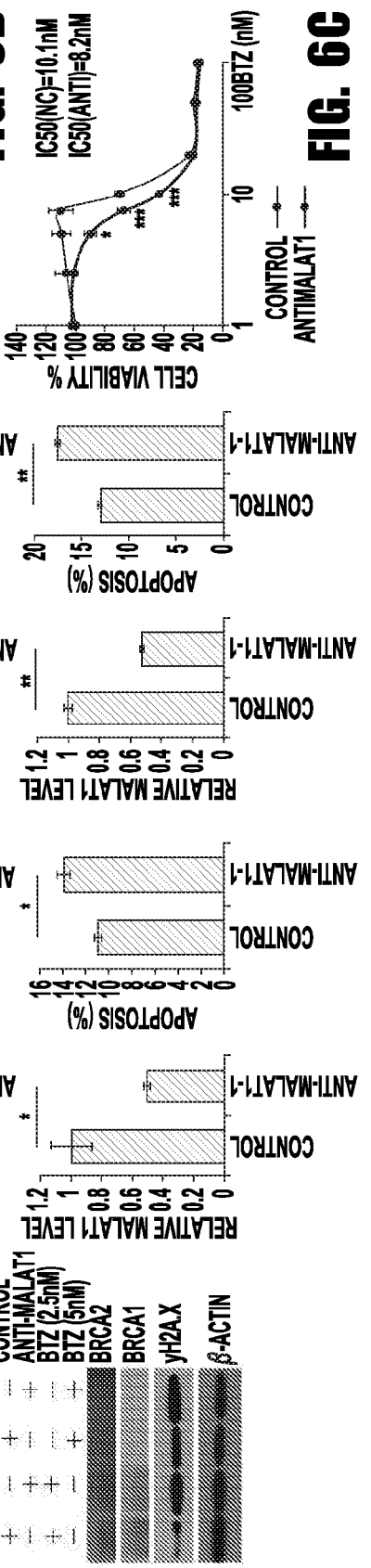
FIG. 6A
FIG. 6B
FIG. 6C

A

B

C

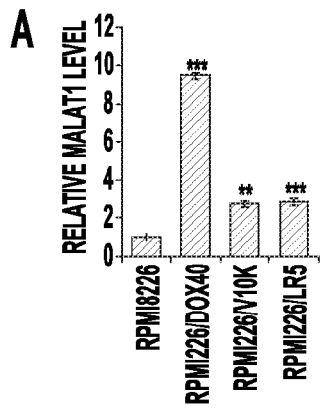
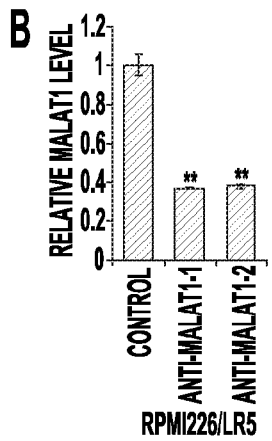
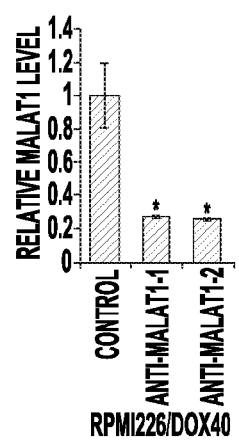
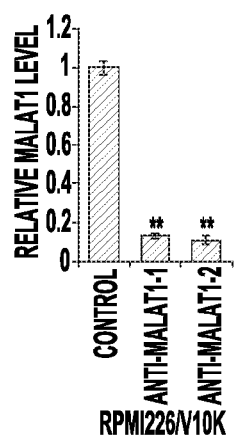
FIG. 14A
FIG. 14B
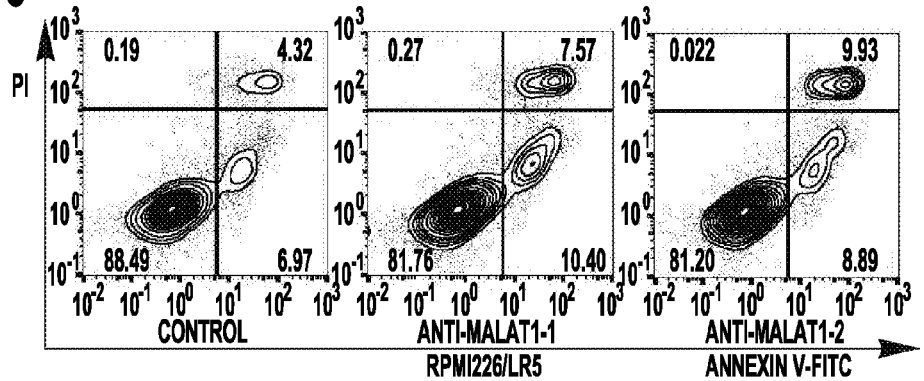
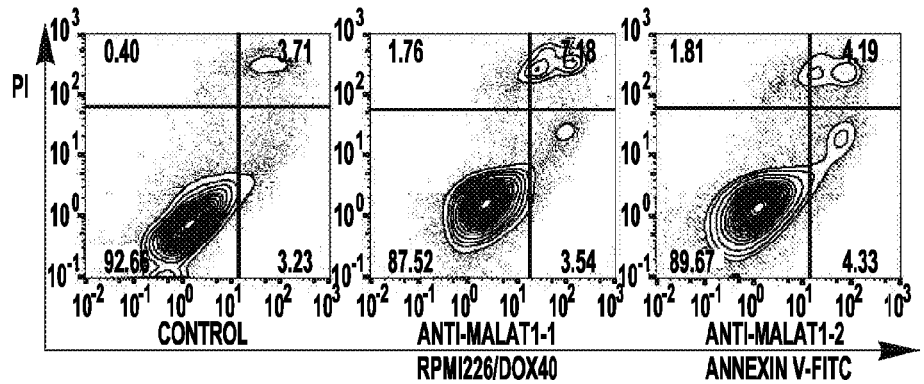
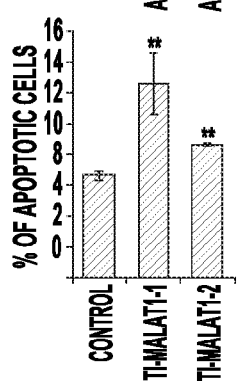
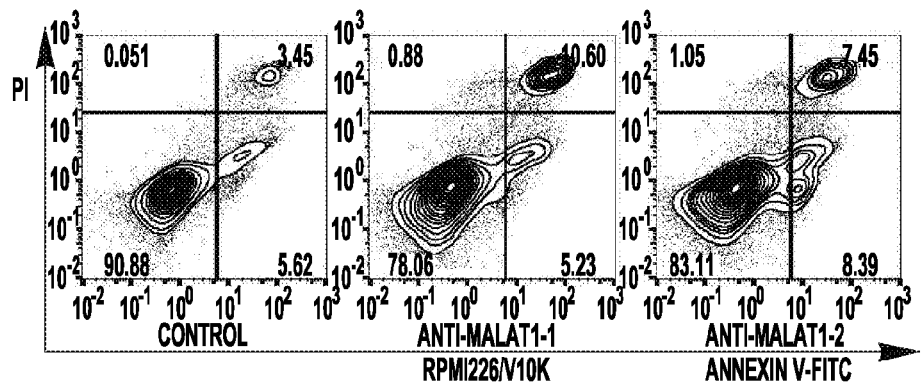
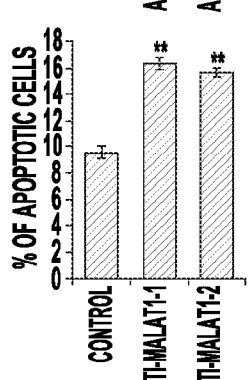
FIG. 14C

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: antisense strand

<400> SEQUENCE: 1
cgaaacattg gcacacagca                                           20

<210> SEQ ID NO 2
<211> LENGTH: 20
<212> TYPE: DNA
<213> ORGANISM: Artificial Sequence
<220> FEATURE:
<223> OTHER INFORMATION: antisense strand

<400> SEQUENCE: 2
ggcauatgca gataauguuc                                           20

<210> SEQ ID NO 3

```
<211> LENGTH: 20
<212> TYPE: DNA
<213> ORGANISM: Artificial Sequence
<220> FEATURE:
<223> OTHER INFORMATION: antisense strand

<400> SEQUENCE: 3
aaggcaagcu gacccugaag                                                20

<210> SEQ ID NO 4
<211> LENGTH: 59
<212> TYPE: DNA
<213> ORGANISM: Artificial Sequence
<220> FEATURE:
<223> OTHER INFORMATION: MALAT1 probe

<400> SEQUENCE: 4
gtgcctttag tgaggggtac ctgaaaaatc ttaaaaaaag cttagcgcc cacctcacc      59

<210> SEQ ID NO 5
<211> LENGTH: 59
<212> TYPE: DNA
<213> ORGANISM: Artificial Sequence
<220> FEATURE:
<223> OTHER INFORMATION: MALAT1 probe

<400> SEQUENCE: 5
tcaaccttta caccgatcta gaatcgaatg cgtagattag ccaggtgcaa accaaaaat    59

<210> SEQ ID NO 6
<211> LENGTH: 20
<212> TYPE: DNA
<213> ORGANISM: Artificial Sequence
<220> FEATURE:
<223> OTHER INFORMATION: primer sequence

<400> SEQUENCE: 6
gttctgatcc cgctgctatt                                                20

<210> SEQ ID NO 7
<211> LENGTH: 22
<212> TYPE: DNA
<213> ORGANISM: Artificial Sequence
<220> FEATURE:
<223> OTHER INFORMATION: primer sequence

<400> SEQUENCE: 7
tcctcaacac tcagccttta tc                                             22

<210> SEQ ID NO 8
<211> LENGTH: 22
<212> TYPE: DNA
<213> ORGANISM: Artificial Sequence
<220> FEATURE:
<223> OTHER INFORMATION: primer sequence

<400> SEQUENCE: 8
caagagcaca agaggaagag ag                                             22

<210> SEQ ID NO 9
<211> LENGTH: 21
<212> TYPE: DNA
<213> ORGANISM: Artificial Sequence
<220> FEATURE:
<223> OTHER INFORMATION: primer sequence

<400> SEQUENCE: 9
```

```
ctacatggca actgtgagga g                                          21

<210> SEQ ID NO 10
<211> LENGTH: 59
<212> TYPE: DNA
<213> ORGANISM: Artificial Sequence
<220> FEATURE:
<223> OTHER INFORMATION: MALAT1 probe

<400> SEQUENCE: 10
gtgcctttag tgaggggtac ctgaaaaatc ttaaaaaaag gcttagcgcc cacctcacc   59

<210> SEQ ID NO 11
<211> LENGTH: 20
<212> TYPE: DNA
<213> ORGANISM: Artificial Sequence
<220> FEATURE:
<223> OTHER INFORMATION: anti-MALAT1 sequence

<400> SEQUENCE: 11
cgaaacattg gcacacagca                                            20

<210> SEQ ID NO 12
<211> LENGTH: 20
<212> TYPE: DNA
<213> ORGANISM: Artificial Sequence
<220> FEATURE:
<223> OTHER INFORMATION: anti-MALAT1 sequence

<400> SEQUENCE: 12
ggcauatgca gataauguuc                                            20

<210> SEQ ID NO 13
<211> LENGTH: 21
<212> TYPE: DNA
<213> ORGANISM: Artificial Sequence
<220> FEATURE:
<223> OTHER INFORMATION: negative control scrambled sequence

<400> SEQUENCE: 13
maaggcaagc ugacccugaa g                                          21
```

CANCER TREATMENT BY MALAT1 INHIBITION

CROSS-REFERENCE TO RELATED APPLICATIONS

This application claims priority to U.S. Provisional Patent Application Ser. No. 62/483,396, filed Apr. 9, 2017, all of which are incorporated herein by reference.

GOVERNMENT FUNDING

This invention was made with Government support under grant number R00 CA172292 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 9, 2018, is named MALAT1_ST25 and is 2,701 bytes in size.

BACKGROUND

Multiple myeloma (MM), a cancer of terminally differentiated plasma cells, is the second most frequently diagnosed hematologic cancer in the United States. MM is nearly always preceded from an age-related progressive pre-malignant condition termed monoclonal gammopathy of undetermined significance (MGUS). The finding of long non-coding RNA (lncRNA) transcripts from genomic regions is one of the most unexpected findings of the genomics era. lncRNAs are a group of RNA transcripts longer than 200 nt that do not encode proteins but are involved in various forms of gene expression regulation. Ntziachristos et al., Nature immunology, 17(9): 1016-1024 (2016). Rapidly accumulating evidences indicate that lncRNAs are involved in the initiation and progression of almost all kinds of cancer, including MM. Evans et al., J Clin Invest., 126(8): 2775-2782 (2016); Ronchetti et al., Oncotarget, 7(12): 14814-14830 (2016) These findings collectively support the possibility that systematic investigation of lncRNA function in tumorigenesis will yield novel insights into diagnosis and treatment of cancers.

Metastasis-associated lung adenocarcinoma transcript 1 (MALAT1), also known as nuclear-enriched noncoding transcript 2 (NEAT2), is a highly conserved nuclear lncRNA (~8.7kb in human). Schmidt et al., J Thorac Oncol, 6(12): 1984-1992 (2011) MALAT1 was initially found to play an important role in nuclear speckles and to interact with pre-mRNA splicing factors in Hela cells through regulating a variety of biological process. West et al., Molecular cell, 55(5): 791-802 (2014) It was originally identified in metastatic non-small cell lung cancer(NSCLC) (Ji et al., Oncogene, 22(39): 8031-8041 (2003) and over-expressed in different types of tumor such as hepatocellular carcinoma (Luo et al., Hepatology, 44(4): 1012-1024 (2006)), breast cancer (Guffanti et al., BMC genomics, 10: 163 (2009)) and prostate cancer (Ren et al., J Urol., 190(6): 2278-2287 (2013)). In MM, MALAT1 is reported to be the most highly expressed lncRNA and correlated with poor prognosis (Ronchetti et al., Oncotarget, 7(12): 14814-14830 (2016)) and significantly unregulated in fatal course extramedullary MM compared with newly diagnosed MM patients. Handa et al., Br J Haematol, 179(3): 449-460 (2017).

SUMMARY

In our current study, we sought to determine the oncogenic role of MALAT1 and explore it as a possible therapeutic target for MM. We found that MALAT1 is highly expressed in MGUS, smoldering MM (SMM) and MM compared to normal plasma cells. We further identified the function of MALAT1 involving in alternative non-homologous end joining (A-NHEJ) pathway through binding with PARP1/LIG3 complex, and regulated apoptosis via co-acting with PARP1. Finally, we developed a novel single-wall carbon nanotube (SWCNT)-conjugated anti-MALAT1 oligo, and used it in two MM xenograft murine models, and observed remarkable therapeutic outcomes.

In one aspect, the invention provides a method of treating cancer in a subject in need thereof, comprising administering a therapeutically effective amount of an oligonucleotide that specifically hybridizes to MALAT1 to the subject. In some embodiments, the oligonucleotide is an antisense oligonucleotide. In a further embodiment, the cancer is selected from the group consisting of breast cancer, lung cancer, prostate cancer, hepatocellular carcinoma, and leukemia. In some embodiments, additional anticancer treatment is provided to the subject. For example, in some embodiments, the method further comprises administering an antitumor agent such as bortezomib to the subject, or administering a PARP1 and/or LIG3 inhibitor to the subject. In some embodiments, the oligonucleotide is administered using a carbon nanotube.

In another aspect, the invention provides an antisense oligonucleotide including from 5 to 30 nucleotides, and being capable of specifically hybridizing to MALAT1. In some embodiments, the antisense oligonucleotide is a phosphorothioate-linked oligonucleotide. In a further embodiment, the oligonucleotide consists of 25 or fewer nucleotides and comprises the nucleotide sequence CGAAACATTGGCACACAGCA (SEQ ID NO: 1), GGCAUAUGCAGATAAUGUUC (SEQ ID NO: 2), or AAGGCAAGCUGACCCUGAAG (SEQ ID NO: 3).

BRIEF DESCRIPTION OF THE FIGURES

FIGS. 1A-1C provide graphs and images showing MALAT1 overexpression promoted the tumorigenesis of MM. (A) $2 \times 10^6$ MALAT1 overexpressed or control MM.1S cells were injected subcutaneously to the shoulder of SCID mice. The sizes of xenograft were measured once a week. Mice were sacrificed 30 days after injection, and xenografts were weighted. (B) MALAT1 level was determined by qRT-PCR. (C) The levels of Ki-67 and c-Caspase3 were detected by immunohistochemistry. ($*p<0.05$, $p<0.01$, $*p<0.001$)

FIGS. 2A-2C provide images showing that PARP1/LIG3 complex was identified as MALAT1 binding target by RAP-MS. (A) Schematic diagram of the RAP-MS strategy used to identify MALAT1 binding proteins. (B) PARP1, LIG3 and XRCCS were verified as MALAT1 binding proteins. (C) MALAT1 co-localized with PARP1 in H929, MM.1S and RPMI8226 cells (scale bar=1 µM).

FIGS. 3A-3C provide graphs and images showing the verification of the binding between MALAT1 and PARP1 by RIP-PCR. (A) Schematic diagram of the RIP-PCR assay. (B) The level of PARP1 before or after RIP was determined by immunoblotting. (C) MALAT1 pulled-down by PARP1 antibody-conjugated beads were determined by qRT-PCR (right panel), left panel is input (*p<0.05, p<0.01, *p<0.001).

FIGS. 4A-4C provide graphs and images showing MALAT1 inhibition induced DNA damage and cell death in MM. 2'-OMe-modified anti-MALAT1 oligos or control oligos were transfected into H929 (A), MM.1S (B) or RPMI8226 (C) cells, respectively. At 48 h after transfection, cells were collected and subjected to qRT-PCR, immunofluorescence staining for γH2A.X, immunoblotting of γH2A.X, PARP1, c-PARP1, caspase-3, and c-caspase3 and apoptosis assay. (*p<0.05, **p<0.01).

FIGS. 6A-6C provide graphs and images showing the synergistic effect of anti-MALAT1 and bortezomib in MM. H929 (A), MM.1S (B) and RPMI8226 (C) cells were transfected with 1 nM anti-MALAT1 or control oligos and treated with bortezomib. Cells were collected for immunoblotting, apoptosis assay and qRT-PCR. Cell viability was measured and IC50 was calculated before and after MALAT1 knockdown.(*p<0.05, p<0.01, *p<0.001)

FIGS. 8A-8C provide graphs and images showing that SWCNT-anti-MALAT1 treatment repressed myeloma growth in both xenograft and disseminated murine models. (A) MM.1S-Luc-GFP cells were injected subcutaneously to SCID mice (5 mice each group). SWCNT-anti-MALAT1 or SWCNT-ctrl was injected into the tumors at the indicated days. Tumor growth was monitored by IVIS. Mice were sacrificed on day 30, tumor samples were subjected to qRT-PCR, WB and immunohistochemistry (Scale bars=100 µM). (B) SCID mice (7 mice each group) were intravenously injected with MM.1S-Luc-GFP cells, then injected with SWCNT-anti-MALAT1 or SWCNT-ctrl once a week through tail veins. Kaplan-Meier analysis indicated SWCNT-anti-MALAT1 prolonged mouse lifespan significantly (P=0.04). (C) Proposed model of MALAT1 antagonist induces MM cell apoptosis.

FIGS. 14A-14C provide graphs showing anti-MALAT1 treatment induced cell apoptosis in drug resistant cell lines. (A) qRT-PCR result of MALAT1 expression levels in RPMI8226 drug-resistant cell lines and their parental RPMI8226 cells. (B) RPMI8226/LR5, RPMI8226/DOX40 and RPMI8226/V10R cells were transfected with 1 nM antiMALAT1-1/2 or control oligos, then MALAT1 expression levels were determined. (C) The apoptosis of these cells were measured by flow cytometry after stained with annexin V and PI, and the number of apoptotic cells were summarized in the histogram. (*p<0.05, p<0.01, *p<0.001)

DETAILED DESCRIPTION

Figures 5A, 5B, 5C:
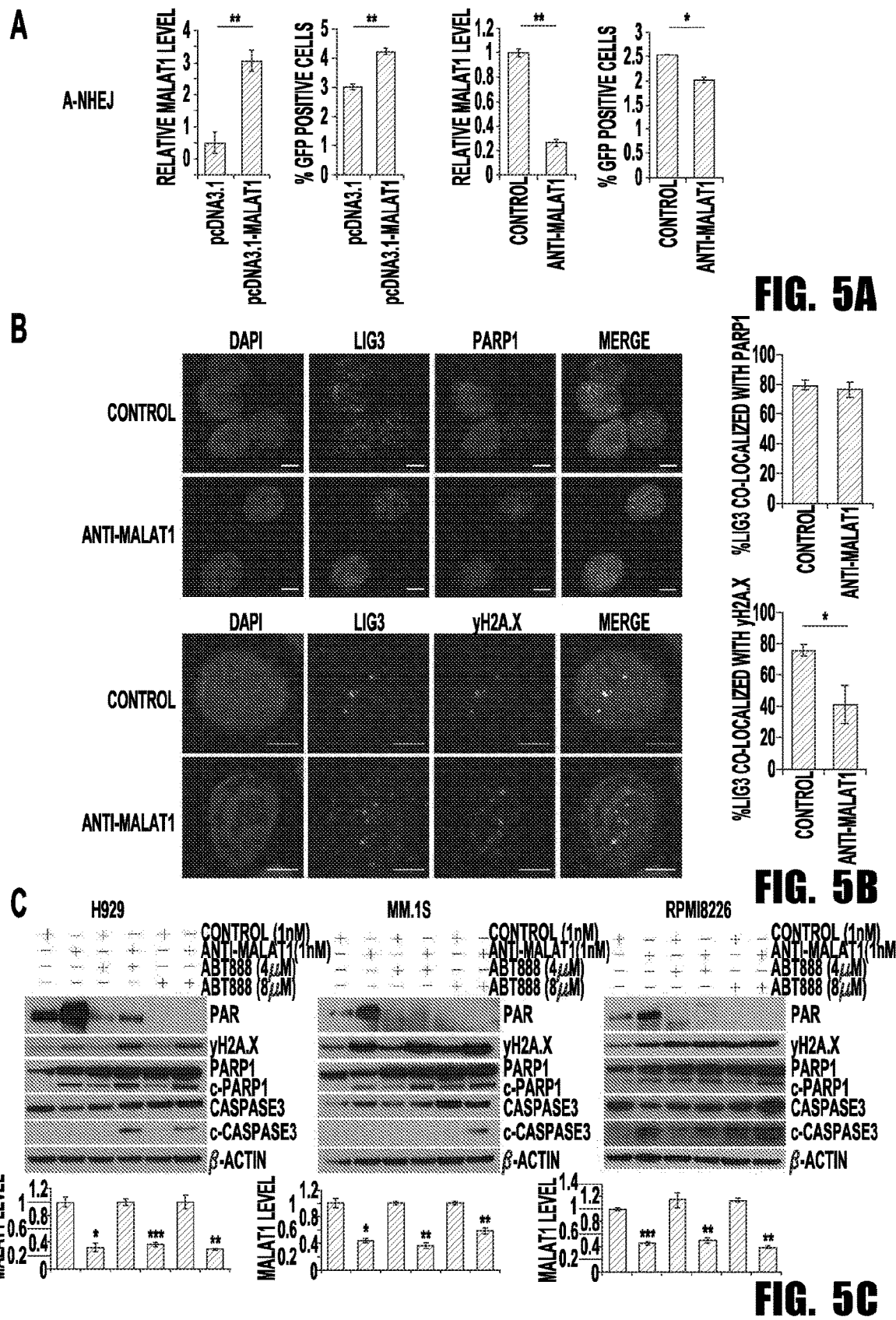
FIGS. 5A-5C provide graphs and images showing MALAT1 coordinated with PAPR1 inhibitor through inhibiting A-NHEJ. (A) In A-NHEJ reporter plasmid (pEJ2-GFP-puro) stable expression 293T cells, pCBA-Scel was transient transfected with MALAT1 overexpression/empty vector or anti-MALAT1/control gapmer. Then GFP positive cells were determined by flow cytometry. (B) The co-localization between LIG3 and PARP1 or γH2A.X were determined by immunofluorescence staining (scale bar=5 µM). (C) H929, MM.1S and RPMI8226 cells transfected with anti-MALAT1 or control oligos were treated with ABT-888. Cells were collected for WB. MALAT1 were determined by qRT-PCR. (*p<0.05, **p<0.01)

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein and in the appended claims, the singular forms "a", "and", and "the" include plural referents unless the context clearly dictates otherwise. Thus, for example, reference to "a sample" also includes a plurality of such samples and reference to "the splicing regulator protein" includes reference to one or more protein molecules, and so forth.

As used herein, the term "about" refers to +/−10% deviation from the basic value.

As used herein the term "nucleic acid" or "oligonucleotide" refers to multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). The term shall also include polynucleosides (i.e. a polynucleotide minus the phosphate) and any other organic base containing polymer. Purines and pyrimidines include but are not limited to adenine, cytosine, guanine, thymidine, inosine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Natural nucleic acids have a deoxyribose- or ribose-phosphate backbone.

An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Other such modifications are well known to those of skill in the art. Thus, the term nucleic acid also encompasses nucleic acids with substitutions or modifications, such as in the bases and/or sugars.

The term "base" encompasses any of the known base analogs of deoxyribonucleic acid (DNA) and ribonucleic acid (RNA). Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides.

The term "antisense oligonucleotide", as used herein, refers to a single-stranded oligonucleotide with a base sequence complementary to a segment of another oligonucleotide that can specifically bind to the target oligonucleotide and inhibit its activity. Antisense oligonucleotides include antisense RNA and antisense DNA, as well as other types of antisense molecules described herein.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Peptide" and "polypeptide" are used interchangeably herein and refer to a compound made up of a chain of amino acid residues linked by peptide bonds. An "active portion" of a polypeptide means a peptide that is less than the full length polypeptide, but which retains measurable biological activity and retains biological detection.

As used herein, the term "tumor" refers to any neoplastic growth, proliferation or cell mass whether benign or malignant (cancerous), whether a primary site lesion or metastases.

As used herein "therapeutically effective amount" refers to an amount of a composition that relieves (to some extent, as judged by a skilled medical practitioner) one or more symptoms of the disease or condition in a mammal. Additionally, by "therapeutically effective amount" of a composition is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. But a determination of a therapeutically effective amount is within the skill of an ordinarily skilled clinician upon the appreciation of the disclosure set forth herein.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment also includes partial or total destruction of the undesirable proliferating cells with minimal destructive effects on normal cells. In accordance with the present invention, desired mechanisms of treatment at the cellular include, but are not limited to one or more of apoptosis, cell cycle arrest, cellular differentiation, or DNA synthesis arrest. A subject at risk is a subject who has been determined to have an above-average risk that a subject will develop cancer, which can be determined, for example, through family history or the detection of genes causing a predisposition to developing cancer.

The term "subject," as used herein, refers to a species of mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos.

As used herein the term "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated.

Unless defined otherwise, all technical and scientific terms used herein have the same meaning as commonly understood by one of ordinary skill in the art to which this invention belongs.

Cancer Treatment by MALAT1 inhibition

In one aspect, the invention provides a method of treating cancer in a subject in need thereof, comprising administering a therapeutically effective amount of an oligonucleotide that specifically hybridizes to MALAT1 to the subject. Because MALAT1 plays an important role in DNA repair and apoptosis in cancer cells, its inhibition can provide an anticancer effect.

Metastasis-associated lung adenocarcinoma transcript 1 (MALAT1) is a highly conserved nuclear long non-coding RNA oligonucleotide. MALAT1 is produced from a precursor transcript from which a long non-coding RNA is derived by RNase P cleavage of a tRNA-like small ncRNA (known as mascRNA) from its 3' end. The sequence of MALAT1 in Homo sapiens has been identified. The first form of MALAT1, referred to as variant 1, has a size of 8,779 base pairs, and has been assigned accession number NR_002819.4. The sequence of MALAT1, variant 1, is incorporated by reference herein. The sequences of two other variants of MALAT1 in Homo sapiens are also known. MALAT1, variant two, has a size of 8,545 base pairs, has been assigned Accession No. NR_144567, and lacks an alternate segment in the 5' region compared to variant 1. MALAT1, variant three, has a size of 8,302 base pairs, and has been assigned Accession No. NR_144568. This variant lacks two alternate segments compared to variant 1. The present invention can make use of any oligonucleotide that specifically hybridizes to MALAT1.

Oligonucleotides such as antisense oligonucleotides are tools for use in inhibiting the expression of target genes in a sequence-specific manner and have found use in functional genomics, target validation, and for therapeutic purposes. In some embodiments, the oligonucleotides are RNA-based oligonucleotides, in which the bases are selected from adenine (A), cytosine (C), guanine (G), and uracil (U). Different types of anti-RNA strategies include, for example, the use of single stranded antisense-oligonucleotides, the triggering of RNA cleavage through catalytically active oligonucleotides referred to as ribozymes, RNA interference induced by small interfering RNA molecules, and oligonucleotides that compete for binding. Accordingly, in some embodiments, the oligonucleotide is an antisense oligonucleotide, while in other embodiments, the oligonucleotide inhibits the binding of MALAT1 to a MALAT1 binding protein, such as PARP1 or LIG3.

With respect to single stranded nucleic acids, particularly antisense oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a RNA molecule, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

One of ordinary skill in the art will understand that degenerate or modified nucleotides are further contemplated but must also be capable of specifically hybridizing to MALAT1 or a specific region thereof. For example, an oligonucleotide could differ from the complementary sequence by three nucleotides, two nucleotides, or preferably one nucleotide, although oligonucleotides having the complementary sequence itself are most preferred.

Suitable oligonucleotides (e.g., antisense oligonucleotides) for use in accordance with the invention can be composed of naturally occurring nucleobases, sugars and internucleoside (backbone) linkages as well as oligonucleotides having non-naturally-occurring portions which function similarly or with specific improved functions. Fully or partly modified or substituted oligonucleotides are often preferred over native forms because of several desirable properties of such oligonucleotides, for instance, the ability to penetrate a cell membrane, good resistance to extra- and intracellular nucleases, high affinity and specificity for the nucleic acid target.

Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkyl-halides. The term base encompasses any of the known base analogs of DNA and RNA.

Some success has been shown with chemically modified nucleotides, for example, alkyl modifications at the 2' position of the ribose. These chemically modified nucleotides have shown improved serum stability, higher target affinity and low toxicity. In some embodiments, deoxyribonucleotide phosphodiester oligonucleotides (i.e., "phosphorothioate oligonucleotides") are suitable for use in accordance with the invention. See Eckstein F., Nucleic Acid Ther., 24(6):374-87 (2014). Methylphosphonate oligonucleotides are noncharged oligomers, in which a nonbridging oxygen atom is replaced by a methyl group at each phosphorus in the oligonucleotide chain. The phosphorothioates in the phosphorothioate diastereomer have improved nuclease stability.

Another class of antisense oligonucleotides contains alkyl modifications at the 2' position of the ribose. Accordingly, in some embodiments, the oligonucleotide is a 2'-O-alkyl antisense oligonucleotide. 2'-O-methyl and 2'-O-methoxy-ethyl RNA are members of this class. 2'-O-alky RNA oligonucleotides do not recruit RNase H, their antisense effect is due, for example, to a steric block of translation. Other antisense oligonucleotides modifications may include, for example, C-5 propyne, 2'-O-aminopropyl, and dipyridophenazine-DPPZ. These oligonucleotides form high melting heteroduplexes with targeted mRNA and induce an antisense effect by a non-RNase H-dependent mechanism.

Suitable oligonucleotides also include embodiments that do not possess the natural phosphate-ribose backbone. Peptide Nucleic Acids (PNAs) are nucleic acid analogues that contain an uncharged, flexible, polyamide backbone comprised of repeating N-(2-aminoethyl) glycine units to which the nucleobases are attached via methylene carbonyl linkers. These oligomers can form very stable duplexes or triplexes with nucleic acids: single or double-strand DNA or RNA. The property of high-affinity nucleic acid binding can be explained by the lack of electrostatic repulsion because of the absence of negative charges on the PNA oligomers. Because PNAs are not substrates for the RNase H or other RNases, the antisense mechanism of PNAs depends on steric hindrance. PNAs can also bind to DNA and inhibit RNA polymerase initiation and elongation, as well as the binding and action of transcription factors, such as nuclear factor κB. PNAs can also bind mRNA and inhibit splicing or translation initiation and elongation.

In one aspect, the invention provides an antisense oligonucleotide capable of specifically hybridizing to MALAT1. Suitable oligonucleotides can be unmodified or chemically modified single-stranded oligonucleotides capable of specifically hybridizing to MALAT1. Suitable antisense oligonucleotides can be from 5 to 30 bases in length, from 10 to 30 bases in length, preferably from 12 to 25 bases in length. In some embodiments, the antisense oligonucleotides are from 12 to 19 bases in length. Examples of suitable antisense oligonucleotides include oligonucleotides consisting of 25 or fewer nucleotides and comprises the nucleotide sequence CGAAACATTGGCACACAGCA (SEQ ID NO: 1), GGCAUAUGCAGATAAUGUUC (SEQ ID NO: 2), or AAGGCAAGCUGACCCUGAAG (SEQ ID NO: 3).

In some embodiments, the antisense oligonucleotide is administered together with a pharmaceutically acceptable carrier. In other embodiments, the antisense oligonucleotide is administered with a carbon nanotube to facilitate delivery of the oligonucleotide. The antisense oligonucleotide can be any of the modified oligonucleotides described herein. For example, in some embodiments, the antisense oligonucleotide is a phosphorothioate-linked oligonucleotide, while in further embodiments, the antisense oligonucleotide is a 2'-O-alkyl antisense oligonucleotide. The oligonucleotides may be obtained by chemical synthesis methods or by recombinant methods. For example, oligonucleotides can be synthesized using a soluble or solid support. See Lönnberg H., Beilstein, J Org Chem., 13:1368-1387 (2017).

Cancer Treatment

The invention provides a method of treating cancer in a subject in need thereof using the oligonucleotides described herein. The term "cancer" refers to a proliferative disorder caused or characterized by a proliferation of cells which have lost susceptibility to normal growth control. Cancers of the same tissue type usually originate in the same tissue, and may be divided into different subtypes based on their biological characteristics. Four general categories of cancer are carcinoma (epithelial cell derived), sarcoma (connective tissue or mesodermal derived), leukemia (blood-forming tissue derived) and lymphoma (lymph tissue derived). Over 200 different types of cancers are known, and every organ and tissue of the body can be affected. Specific examples of cancers that do not limit the definition of cancer can include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. Alternatively, a cancer can be multicentric or of unknown primary site (CUPS).

Overexpression of MALAT1 has been demonstrated to be related to poor prognosis in a variety of different types of cancer. Examples of cancer in which MALAT1 overexpression has been demonstrated include breast cancer, lung cancer, prostate cancer, hepatocellular carcinoma, and leukemia. Overexpression of MALAT1 has also been demonstrated to be related to poor prognosis in multiple myeloma. Multiple myeloma, also known as plasma cell myeloma, is a cancer of plasma cells, a type of white blood cell normally responsible for producing antibodies, and is therefore a type of leukemia. In some embodiments, the method of the invention is directed to treatment of types of cancer in which MALAT1 has been demonstrated to be related to poor prognosis, such as multiple myeloma.

In some embodiments, the method is used to treat drug-resistant cancer. Drug-resistant cancer has the ability to resist the effect of drugs that would normally inhibit the growth of the cancer. In some embodiments, the drug-resistant cancer is multidrug resistant cancer. Cancer treatment involving decreasing MALTA1 expression has the ability to circumvent many mechanisms of drug resistance, thereby providing an alternative avenue for cancer treatment.

Treatment includes therapy that provides a result which substantially decreases the level or expression of MALAT1, including for example, an about 20% reduction, preferably an about 25% reduction, more preferably an about 30% reduction, even more preferably an about 33% reduction, even more preferably an about 50% reduction, even more preferably an about 67% reduction, even more preferably an about 80% reduction, even more preferably an about 90% reduction, even more preferably an about 95% reduction, even more preferably an about 99% reduction, even more preferably an about 50 fold reduction, even more preferably an about 100 fold reduction, even more preferably an about 1,000 fold reduction, even more preferably an about 10,000 fold reduction, and most preferable complete inhibition of MALAT1.

Methods in accordance with the invention include administration of the oligonucleotides alone, or combination therapies wherein the animal is also undergoing one or more cancer therapies selected from the group consisting of surgery, chemotherapy, radiotherapy, thermotherapy, immunotherapy, hormone therapy and laser therapy.

In general any combination therapy will include one or more of chemotherapeutics, targeting agents like antibodies; kinase inhibitors; hormonal agents and the like. Combination therapies can also include conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, anti-cancer agents that are well known in the art and can be used as a treatment in combination with the compositions described herein include, but are not limited to As used herein, a first line "chemotherapeutic agent" or first line chemotherapy is a medicament that may be used to treat cancer, and generally has the ability to kill cancerous cells directly.

Examples of chemotherapeutic agents include alkylating agents, antimetabolites, natural products, hormones and antagonists, and miscellaneous agents. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-niercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel (Abraxane) and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (czs-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib. In some embodiments, the additional cancer therapy is bortezomib administration.

In some embodiments, the method also includes administration of an inhibitor of a MALAT1 binding protein. The inventors identified 23 different MALAT1 binding proteins, shown in Table 1 herein. Two MALAT1 binding proteins that were shown to form a complex with MALAT1 are poly (ADP-ribose polymerase (PARP1) and DNA Ligase III (LIG3). Accordingly, in some embodiments, the method further comprises administering a PARP1 and/or LIG3 inhibitor to the subject.

In some embodiments, the method further comprises administering a PARP1 inhibitor to the subject. A variety of PARP1 inhibitors are known to those skilled in the art. See Fu et al., Sci Rep., 6(1), 3 (2016) and Malyuchenko et al., Acta Naturae., 7(3):27-37 (2015). In some embodiments, the PARP1 inhibitor is selected from the group consisting of olaparib, rucaparib, BMN-673, niraparib, and iniparib. In further embodiments, the method comprises administering a LIG3 inhibitor to the subject. A variety of LIG3 inhibitors are known to those skilled in the art. See Chen et al., Cancer Res. 68(9), 3169-3177 (2008) and Tomkinson et al., Transl. Cancer Res. 2(3), pii: 1219 (2013). In some embodiments, the LIG3 inhibitor is L67 or L189, the structures of which are shown below.

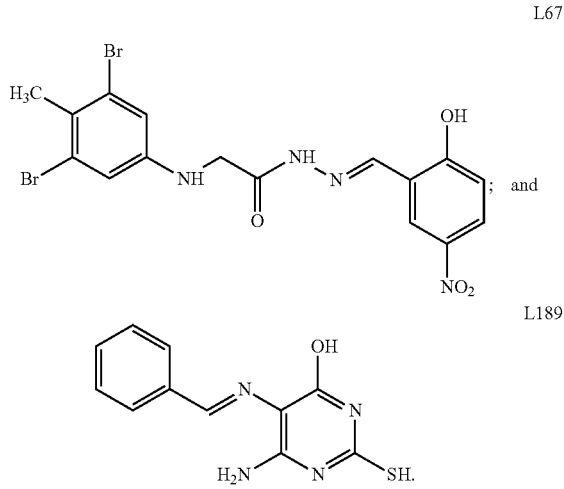

Kits

Kits comprising a pharmaceutical composition comprising an isolated RNA molecule as described herein are also provided. For example, a kit can comprise unit dosage forms of the isolated RNA molecule, and a package insert containing instructions for use of the composition in treatment of a cancer. In some embodiments, the kit comprises a unit dosage form of the isolated RNA molecule, and at least one pharmaceutically acceptable vehicle. The instructions for use in the kit may be for treating a cancer. In some embodiments, the kit comprises the isolated RNA molecule or pharmaceutical composition comprising the isolated RNA molecule as described herein. In some embodiments, the kit comprises instructions for use of the isolated RNA molecule or pharmaceutical composition comprising the isolated RNA molecule in the treatment of cancer, such as, but not limited to, any of the cancers discussed above.

Pharmaceutical compositions (including, for example, formulations and unit dosages) comprising the isolated RNA molecules as described herein, can be prepared and placed in an appropriate container, and labeled for treatment of a cancer. Accordingly, provided is also an article of manufacture, such as a container comprising a unit dosage form of the isolated RNA molecule as described herein, and a label containing instructions for use of the isolated p RNA molecule. In some embodiments, the article of manufacture is a container comprising a unit dosage form of the isolated RNA molecule, and at least one pharmaceutically acceptable vehicle. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of a cancer. It should be understood that the active ingredient may be packaged in any material capable of improving chemical and physical stability.

Oligonucleotide Formulation and Administration

In order for an oligonucleotide (e.g., antisense oligonucleotide) to down-regulate gene expression, it must penetrate into the targeted cells. Uptake occurs through active transport, which in turn depends on temperature, the structure and the concentration of the oligonucleotide, and the cell line. Without desiring to be bound by any theories of the mechanism of action, it is believed that adsorptive endocytosis and fluid phase pinocytosis are the major mechanisms of oligonucleotide internalization, with the relative proportions of internalized material depending on oligonucleotide concentration. At relatively low oligonucleotide concentration, it is likely that internalization occurs via interaction with a membrane-bound receptor. At relatively high oligonucleotide concentration, these receptors are saturated, and the pinocytotic process assumes larger importance.

The use of vectors in delivery of oligonucleotides in accordance with the invention is optional. Clinical trials with antisense oligonucleotides can be carried out with naked oligonucleotides. However to improve cellular uptake and oligonucleotide spatial and temporal activity, a range of techniques and vectors have been developed. Suitable vectors include liposomes, which are vesicular colloid vesicles generally composed of bilayers of phospholipids and cholesterol. Liposomes can be neutral or cationic, depending on the nature of the phospholipids. The oligonucleotide can be easily encapsulated in the liposome interior, which contains an aqueous compartment, or be bound to the liposome surface by electrostatic interactions. These vectors, because of their positive charge, have high affinity for cell membranes, which are negatively charged under physiological conditions. As these vectors use the endosomal pathway to deliver oligonucleotides into cells, certain "helper" molecules have been added into the liposomes to allow the oligonucleotides to escape from the endosomes; these include species such as chloroquine and 1,2-dioleoyl-sn-glycero-3-phosphatidylethanolamine. These "helper" molecules ultimately induce endosomal membrane destabilization, allowing leakage of the oligonucleotide, which then appears to be actively transported in high concentration to the nucleus. Many commercial vectors, such as Lipofectin and compounds known collectively as Eufectins, Cytofectin, Lipofectamine, etc., are commonly used in laboratory research studies. With some of these delivery vehicles, and under defined conditions, oligonucleotide concentrations of <50 nm may be successfully used. The use of other cationic polymers, including, e.g., poly-L-lysine, PAMAM dendrimers, polyalkylcyanoacrylate nanoparticles, CPPs, and polyethyleneimine, are also suitable for use in accordance with the invention.

All of these cationic delivery systems internalize oligonucleotides via an endocytotic mechanism. To avoid the resulting compartmentalization problems, consideration has been given to modulating plasma membrane permeability. By using basic peptides, one can increase oligonucleotide passage through the plasma membrane by a receptor- and transporter-independent mechanism. As these peptides have membrane translocation properties, covalent coupling with an oligonucleotide can increase the latter's penetration into the cell, delivering them directly into the cytoplasm and hence ultimately the nucleus.

An additional suitable approach to oligonucleotide internalization is to generate transient permeabilization of the plasma membrane and allow naked oligonucleotides to penetrate into the cells by diffusion. This approach involves the formation of transitory pores in the membrane, induced either chemically by streptolysin O permeabilization, mechanically by microinjection or scrape loading, or produced by electroporation.

In some embodiments, the oligonucleotide is administered together with a carbon nanotube (CNT). Single walled nanotubes (SWNTs) and multi-walled carbon nanotubes (MWNTs) are cylindrical tubes of $sp^2$ carbon, conceptualized by rolling up single- or multi-layered graphene sheets, respectively. CNTs include both SWNTs and MWNTs. Functionalized, water-soluble CNTs are able to enter cells and delivery oligonucleotides. CNTs can be functionalized to improve their water solubility by a variety of different methods, including oxidation, being wrapped in DNA, and being coated by surfactants and amphiphilic polymers. Examples of functionalized CNTs include those functionalized with ammonia or lysine (Singh et al., J. Am Chem. Soc., 127, 4388-4396 (2005)), polyethyleneimine and cationic pyridinium (Varkouhi et al., Int. J. Pharmaceutics, 416, 419-525 (2011), and those functionalized with siRNA or ssDNA, which can include the oligonucleotide being delivered. Bartholomeusz et al., Nano Res. 2, 279-291 (2009).

Oligonucleotides and conjugates thereof can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Oligonucleotide compositions are generally provided in a formulation with a carrier, such as a pharmaceutically acceptable carrier. Typically, the carrier will be liquid, but also can be solid, or a combination of liquid and solid components. The carrier desirably is a physiologically acceptable (e.g., a pharmaceutically or pharmacologically acceptable) carrier (e.g., excipient or diluent). Physiologically acceptable carriers are well known and are readily available. Suitable pharmaceutical excipients include stabilizers, antioxidants, osmolality adjusting agents, buffers, and pH adjusting agents. Suitable additives include physiologically biocompatible buffers, additions of chelants or calcium chelate complexes, or, optionally, additions of calcium or sodium salts. Pharmaceutical compositions can be packaged for use in liquid form, or can be lyophilized. Preferred physiologically acceptable carrier media are water, buffered water, normal saline, 0.4% saline, 0.3% glycine, hyaluronic acid and the like. The choice of carrier will be determined, at least in part, by the location of the target tissue and/or cells, and the particular method used to administer the composition.

The composition can be formulated for administration by a route including intravenous, intraarterial, intramuscular, intraperitoneal, intrathecal, epidural, topical, percutaneous, subcutaneous, transmucosal (including, for example, pulmonary), intranasal, rectal, vaginal, or oral. The composition also can comprise additional components such as diluents, adjuvants, excipients, preservatives, and pH adjusting agents, and the like.

Formulations suitable for injectable administration include aqueous and nonaqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, lyoprotectants, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, or tablets.

In preferred embodiments, the oligonucleotides can be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the antisense oligonucleotides can be prepared by such methods as described in Rezler et al., J. Am. Chem. Soc. 129(16): 4961-72 (2007); Samad et al., Curr. Drug Deliv. 4(4): 297-305 (2007); and U.S. Pat. Nos. 4,485,045 and 4,544,545. Liposomes with enhanced circulation time are disclosed in U.S. Pat. No. 5,013,556. Albumin nanoparticles are particularly preferred in the compositions of the present invention.

Particularly useful liposomes can be generated by, for example, the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Polynucleotides of the present invention can be conjugated to the liposomes using methods as described in Werle et al., Int. J. Pharm. 370(1-2): 26-32 (2009).

The invention further provides for the use of cell-penetrating peptides (CPPs) to facilitate the delivery of the antisense molecules disclosed herein. CPPs are peptides that are able to efficiently penetrate cellular lipid bilayers. Because of this feature, they can be used to obtain alterations in gene expression. CPPs have been utilized in in vivo and in vitro experiments as delivery vectors for different bioactive cargoes. In particular, CPPs have been used as vectors for multiple effectors of gene expression such as oligonucleotides for antisense, siRNA (small interfering RNA) and decoy dsDNA (double-stranded DNA) applications, and as transfection agents for plasmid delivery. Any suitable conjugation method may be employed to couple the CPP and the oligonucleotide (Heitz et al., Br J. Pharmacol. 2009 157(2): 195-206.) Suitable CPPs include, but are not limited to, Tat, Penetratin, Transportan, VP-22, MPG, Pep-1, MAP, PPTG1, SAP, Oligoarginine, SynB, Pvec, and hCT (9-32) (Heitz et al., Br J. Pharmacol. 2009 157(2):195-206.).

In other embodiments, a composition can be delivered using a natural virus or virus-like particle, a dendrimer, carbon nanoassembly, a polymer carrier, a paramagnetic particle, a ferromagnetic particle, a polymersome, a filomicelle, a micelle or a lipoprotein.

Administration into the airways can provide either systemic or local administration, for example to the trachea and/or the lungs. Such administration can be made via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or noon-aerosol spray of a liquid. Pressurized packs can comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhalator or insufflator.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhaled aerosols, rectal or vaginal suppositories, mouthwashes, rapidly dissolving tablets, or lozenges. For transdermal administration, the active compounds are formulated into ointments, salves, gels, foams, or creams as generally known in the art.

The pharmaceutical compositions can be delivered using drug delivery systems. Such delivery systems include hyaluronic acid solutions or suspensions of collagen fragments. The drugs can be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl) methylacrylamide] and the like. Particular formulations using drug delivery systems can be in the form of liquid suspensions, ointments, complexes to a bandage, collagen shield or the like.

Pharmaceutical compositions of the invention can be administered in a single dose or in multiple doses. Where the administration of such a composition is by infusion, the infusion can be a single sustained dose or can be delivered by multiple infusions. Injection of the agent can be directly into the tissue at or near the site of aberrant target gene expression. Multiple injections of the agent can be made into the tissue at or near the site.

Dosage levels on the order of about 1 µg/kg to 100 mg/kg of body weight per administration are useful in the treatment of a disease. In regard to dosage, an compositions of the present invention can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of antisense composition per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of antisense composition per kg of bodyweight. The unit dose, for example, can be administered by injection (e.g., intravenous or intramuscular, intrathecally, or directly into an organ), inhalation, or a topical application.

One skilled in the art can also readily determine an appropriate dosage regimen for administering the antisense composition of the invention to a given subject. In some embodiments, the compositions are administered once or twice daily to a subject for a period of from about three to about twenty-eight days, more preferably from about seven to about ten days. In further embodiments, the unit dose is administered less frequently than once a day, e.g., less than every 2, 4, 8 or 30 days. In other embodiments, the unit dose is not administered with a frequency (e.g., not a regular frequency). In another embodiment, the unit dose is not administered with a frequency (e.g., not a regular frequency). In other embodiments, the antisense composition can be administered to the subject once, as a single injection or deposition at or near the site on unwanted target nucleic acid expression. Because oligonucleotide agent-mediated up-regulation can persist for several days after administering the antisense composition, in many instances, it is possible to administer the composition with a frequency of less than once per day, or, for some instances, only once for the entire therapeutic regimen.

Where a dosage regimen comprises multiple administrations, it is understood that the effective amount of antisense composition administered to the subject can include the total amount of antisense composition administered over the entire dosage regimen. One skilled in the art will appreciate that the exact individual dosages may be adjusted somewhat depending on a variety of factors, including the specific antisense composition being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration.

The following example is included for purposes of illustration and is not intended to limit the scope of the invention.

EXAMPLES

Targeting the MALAT1/PARP1/LIG3 Complex Induces DNA Damage and Apoptosis in Multiple Myeloma Metastasis-associated lung adenocarcinoma transcript 1(MALAT1) is a highly conserved long non-coding RNA (lncRNA). Overexpression of MALAT1 has been demonstrated to related to poor prognosis of multiple myeloma (MM) patients. Here, we demonstrated that MALAT1 plays important roles in MM DNA repair and cell death. We found bone marrow plasma cells from patients with monoclonal gammopathy of undetermined significance (MGUS) and MM express elevated MALAT1 and involve in alternative-non-homozygous end joining (A-NHEJ) pathway by binding to PARP1 and LIG3, two key components of the A-NHEJ protein complex. Degradation of the MALAT1 RNA by RNase H using antisense gapmer DNA oligos in MM cells stimulated poly-ADP-ribosylation of nuclear proteins, defected the DNA repair pathway, and further provoked apoptotic pathways. Anti-MALAT1 therapy combined with PARP1 inhibitor or proteasome inhibitor in MM cells showed a synergistic effect in vitro. Furthermore, using novel single wall carbon nanotube (SWCNT) conjugated with anti-MALAT1 oligos, we successfully knocked down MALAT1 RNA in cultured MM cell lines and xenograft murine models. Most importantly, anti-MALAT1 therapy induced DNA damage and cell apoptosis in vivo, indicating that MALAT1 could serve as a potential novel therapeutic target for MM treatment.

Methods

Cell Lines, Plasmids and Human MM Tissues

Human MM cell lines including MM.1S, H929, RPMI8226 and HEK293T were obtained from ATCC. Bortezomib-resistant (RPMI8226/V10R) cell line is a kind gift of Dr. Robert Orlowski (The University of Texas M.D. Anderson Cancer Center, Houston, Tex., USA). Melphalan-resistant (RPMI8226/LR5) and doxorubicin-resistant (RPMI8226/DOX40) cell lines are gift from Dr. William Dalton (Moffitt Cancer Center, Tampa, Fla.). Bone marrow (BM) plasma cells were isolated from four healthy donors (HDs) and 7 MM patients using CD138 magnetic beads (Miltenyi Biotec). Total RNA was isolated using Trizol reagent (Thermo Fisher Scientific). To establish A-NHEJ, NHEJ and homologous recombination (HR) DNA repair pathway reporter stable cell lines, pEJ2GFP-puro (#44025, Addgene) (Bennardo et al., PLoS Genet; 4(6): e1000110 (2008), pimEJ5GFP(#44026, Addgene) (Bennardo et al., ibid) and pDRGFP (#26475, Addgene) (Pierce et al., Genes Dev, 13(20): 2633-2638 (1999)) vectors were transfected into HEK293T cells separately and selected with 2 µg/mL puromycin. To construct the MALAT1 overexpression vector, full length of human MALAT1 cDNA was cloned into pCDH-MSCV-MCS-EF1-copGFP-T2A-Puro plasmid (System Biosciences), between NotI and SwaI sites. The packaging system was used according to the manufacturer's protocol. MM.1S cells were infected by MALAT1 overexpression (V-MALAT1) or empty control virus (V-ctrl), and subjected to flow sorting by flow cytometry using green fluorescent protein copGFP as a marker.

Formalin-fixed paraffin-embedded (FFPE) BM blocks of 11 HDs and 9 MM patients were obtained from the myeloma tissue bank of the Cleveland Clinic Taussig Cancer Institute and the Norman Bethune International Peace Hospital. All participants signed informed consent forms. This study was approved by institutional review boards (IRB) of both Cleveland Clinic and Norman Bethune International Peace Hospital. MM tissue microarray (TMA) was purchased from US Biomax, Inc (T291b), which contained BM from 2 HDs and 4 MM patients.

RNA Antisense Purification (RAP)

Nuclear extracts were incubated with a 59bp biotin-labeled MALAT1 probe GTGCCTTTAGT-GAGGGGTACCTGAAAAATCTTAAAAAAAGGCT-TAGCGCCCACCT CACC/3Bio/ (SEQ ID NO: 4) or sequence-scrambled probe TCAACCTTTACACC-GATCTAGAATCGAATGCGTAGATT-AGCCAGGTGCAAACCAA AAAT/3Bio/ (SEQ ID NO: 5) and hybridized at 4° C. for 2 hours. Hybridized material was captured with magnetic streptavidin beads (Thermo Fisher Scientific). Bound material was washed and eluted with RNaseH (New England Biolabs) as previously described.

West et al., Molecular cell, 55(5): 791-802 (2014) The proteins were separated by SDS-PAGE and stained using Coomassie blue. Specific bands were isolated for whole proteomic mass spectrometry (MS) analysis.

Ribonucleoprotein Immunoprecipitation (RIP)

$2\times10^7$ H929 or MM.1S cells were rinsed with PBS and then irradiated with 150 mJ/cm² at 254 nm using a UV cross-linker. Cell pellets were resuspended in 100 µL cytoplasmic extract(CE) buffer (10 mM HEPES, 60 mM KCl, 1 mM EDTA, 0.075% NP40, 1 mM DTT, pH 7.6). The cells were incubated on ice for 3 min and then centrifuged at 250 g for 5 min. The cell nuclei were washed with 500 µL CE buffer without NP40 and then resuspended in lysis buffer (150 mM NaCl, 50 mM Tris-HCl pH 7.5, 0.5% Triton X-100 supplemented with protease inhibitor cocktail and RNase inhibitor). The lysate was sonicated for 5 min with 30 sec on/off intervals on ice, and then centrifuge at 14,000 g for 10 minutes. The cell lysate was further diluted(1:5) with NT2 buffer (50 mM Tris-HCl pH7.4, 150 mM NaCl, 1 mM $MgCl_2$, 0.05% NP-40 supplemented with fresh 200U RNaseOut, 400 µM VRC, 1mM DTT, 20 mM EDTA, and protease inhibitor cocktail).

Protein A/G magnetic beads (Pierce protein A/G magnetic beads; Thermo scientific) were washed with NT2 buffer 6 times and then pre-coated using 5% BSA NT2 buffer (1:5 v/v) at room temperature for 1 h. anti-PARP1 or anti-LIG3 antibody, 2 µg, was added to 500 µL of the bead mixture and incubated at 4° C. for 12 hours. The beads were washed in ice-cold NT2 buffer for 5 times and resuspended in 850 µL NT2 buffer.

The cell lysate was mixed with the antibody-coated beads, and an aliquot of the mixture was removed for total RNA and protein determination. The remaining lysate was incubated with beads at 4° C. for 4 hours. After co-IP, the beads were washed as follows: twice with lysis buffer; thrice with the lysis buffer containing 900 mM NaCl and 1% NP-40; and twice more with lysis buffer. The beads were then transferred to a fresh tube and subjected to a final wash with the lysis buffer containing 0.05% NP-40. Following the washes, an aliquot of beads was removed from each sample and mixed with 2×LDS sample buffer for western blot analysis. Another aliquot of beads was used for RNA extraction.

Cell Culture and Treatment

Human MM cell lines (H929, MM.1S and RPMI8226) and drug-resistant cell lines (RPMI8226/DOX40, RPMI8226/LR5 and RPMI8226/V10R) were maintained in RPMI 1640 medium containing 10% fetal bovine serum (FBS), 100 U/mL penicillin, and 100 µg/mL streptomycin.

For anti-MALAT1 transfection and ABT-888 (Santa Cruz Biotechnology Inc) or bortezomib (MilliporeSigma) treatment, MM cells were seeded on 12-well plates at a concentration of $5\times10^5$ cells/mL. The cells were transfected using Lipofectamine 2000 (Thermo Fisher Scientific) with 1 nM control or anti-MALAT1 oligos for 24 hours and then treated with a gradient concentration of ABT-888 or bortezomib for another 24 hours. Cells were subjected to proliferation and apoptosis assays, qRT-PCR, and immunoblotting.

For the drug resistant cells, RPMI8226/DOX40, RPMI8226/LR5 and RPMI8226/V10R cells were transfected with 1 nM control or anti-MALAT1 oligos separately for 24 hours and treated with a gradient concentration of doxorubicin for RPMI8226/DOX40, or melphalan for RPMI8226/LR5, or bortezomib for RPMI8226/V10R for 72 hours. Cell were subjected to qRT-PCR, proliferation and apoptosis assays.

Immunohistochemistry

Formalin-fixed, paraffin-embedded (FFPE) sections of bone marrow biopsy specimens from patients with MM and healthy donors, and tissue arrays (US Biomax) were deparaffinized and then incubated with mouse anti-CD138 primary antibody (Santa Cruz Biotechnology Inc, sc-12765) at 4° C. overnight. After incubation with HRP conjugated goat anti-mouse secondary antibody, the detection of signal was achieved using DAB Substrate kit (Abcam, ab64238) following the manufacture's instruction. Images were obtained using a microscopy (Leica DM2000 LED) and a digital camera (Leica DMC 2900). Three different random images were captured for each sample at 400× magnification and the relative density of CD138 signal was quantified by Image J. The results were analyzed by student's t-test and $p\leq0.05$ was statistically significant.

Quantitative RT-PCR

Quantitative RT-PCR (qRT-PCR) analysis was used to determine the relative expression level of MALAT1. Total RNA was extracted from cells or tissues using Trizol Reagent (Thermo Fisher Scientific) according to the manufacturer's instructions. After Turbo DNase (Thermo Fisher Scientific) treatment, 500 ng total RNA was subjected to reverse transcription using the RevertAid first-stand cDNA synthesis kit (Thermo Fisher Scientific). Quantitative PCR using SYBR Green PCR master mix (Thermo Fisher Scientific) was employed to determine MALAT1 level with PCR cycle conditions of 95° C. 10 min, 95° C. 15 s, and 60° C. 1 min, for 40 cycles. GAPDH was used as loading control. Primer sequences were:

```
MALAT1-QF:
                            (SEQ ID NO: 6)
5'-GTTCTGATCCCGCTGCTATT-3'

MALAT1-QR:
                            (SEQ ID NO: 7)
5'-TCCTCAACACTCAGCCTTTATC-3'

GAPDH-QF:
                            (SEQ ID NO: 8)
5'-CAAGAGCACAAGAGGAAGAGAG-3'

GAPDH-QR:
                            (SEQ ID NO: 9)
5'-CTACATGGCAACTGTGAGGAG-3'
```

Immunoblotting

Protein was extracted from cells using RIPA buffer (Thermo Fisher Scientific) containing protease inhibitor cocktail (Roche) and phosphatase inhibitor cocktail (Thermo Fisher Scientific). Protein extracts were boiled in SDS/β-mercaptoethanol sample buffer, and 30 µg samples were loaded into each well on 4%-12% polyacrylamide gels (Thermo Fisher Scientific). The proteins were separated by electrophoresis, and the proteins in the gels were blotted onto PVDF membranes (Thermo Fisher Scientific) by electrophoretic transfer. The membranes were incubated with mouse anti-PADPR monoclonal antibody (#ab14459, Abcam), rabbit anti-phosphor-histone H2A.X (Ser139) polyclonal antibody (Cell Signaling, #2577), rabbit anti-PARP1 monoclonal antibody (Cell Signaling, #9532), rabbit anti-caspase-3 polyclonal antibody (Cell Signaling, #9662), rabbit anti-cleaved caspase-3 monoclonal antibody (Cell Signaling, #9664), rabbit anti-RIP monoclonal antibody (Cell Signaling, #3493), rabbit anti-LC3B polyclonal antibody (Cell Signaling, #2775), rabbit anti-BRCA1 monoclonal antibody (Cell Signaling, #14823), rabbit anti-BRCA2 (Abcam, #ab123491), mouse anti-DNA ligase III monoclonal antibody (Santa Cruz Biotechnology Inc., sc-56089), rabbit anti-MRE11 monoclonal antibody (Cell Signaling, #4847), rabbit anti-NBS1 monoclonal antibody (Cell Signaling, #14956), rabbit anti-phospho-ATR polyclonal antibody (GeneTex, GTX128145), mouse anti-XRCC5 monoclonal antibody (Abcam, ab119935), mouse anti-phospho-ATM monoclonal antibody (Cell Signaling, #4526), rabbit anti-CtIP polyclonal antibody (Bethyl Laboratories, 300-488A), rabbit anti-Rad50 polyclonal antibody (Cell Signaling, #3427), goat anti-XRCC6 antibody (Santa Cruz, S.C.-1487) or goat anti-β-actin polyclonal antibody (Santa Cruz Biotechnology Inc., sc-1615) overnight at 4° C. The specific protein—antibody complex was detected with horseradish peroxidase-conjugated rabbit anti-mouse IgG. Detection by chemiluminescence reaction was carried using the SuperSignal West Femto Maximum Sensitivity Substrate kit (Thermo Fisher Scientific). β-actin was used as a loading control.

MALAT1 in situ hybridization

Slides were deparaffinized and rehydrated through immersion in xylene and an ethanol gradient and then digested with 20 μg/mL proteinase K in pre-warmed 50 mM Tris for 20 min at 37° C. After fixation in 4% paraformaldehyde for 5 min at room temperature, slides were dehydrated by immersion in an ethanol gradient and air dried; slides were pre-hybridized using DIG Easy Hyb (Roche, Mannheim, Germany) at 50° C. for 1 h. The 10 pmol digoxin-labeled MALAT1 DNA probe GTGCCTTTAGTGAGGGGTACCT-GAAAAATCTTAAAAAAAGGCTTAGCGCCCACCT CACC/3Dig_N/(SEQ ID NO: 10) was denatured in hybridization buffer at 95° C. for 2 min and then chilled on ice. The MALAT1 probe was diluted in 250 μL pre-warmed in hybridization buffer.

Each sample was covered with 50-100 μL diluted probe and incubated in a humidified hybridization chamber at 50° C. overnight. Slides were washed twice in 50% formamide in 4× SSC at 37° C. for 30 min, and then washed three times in 2× SSC at 37° C. for 15 min. After twice washing with maleic acid buffer containing Tween-20 (MABT), slides were blocked using blocking buffer (Roche) at room temperature for 30 min, the blocking buffer was drained off, and the samples were incubated with 1:250 diluted anti-digoxigenin-AP fab fragments (Roche) at 37° C. for 1h. After washing twice in MABT and once in detection solution (0.1M Tris-HCl, 0.1M NaCl, pH9.5), the slides were stained with freshly diluted NBT/BCIP detection solution (Roche) and incubated at 37° C. for 30 min. Slides were washed in PBS twice, air dried for 30 min, and then mounted with Eukitt quick-hardening mounting medium (Sigma Aldrich, St. Louis, Mo., USA). Images were obtained using a microscopy (Leica DM2000 LED) and a digital camera (Leica DMC 2900). Three different random images were captured for each sample at 400× magnification and the relative density of MALAT1 signal was quantified by Image J. The results were analyzed by student's t-test and $p<0.05$ was statistically significant.

Mass Spectrum (MS) Analysis

The protein bands were cut from the gel as closely as possible to each band, washed/destained in 50% ethanol, 5% acetic acid, and then dehydrated in acetonitrile. The bands were then reduced with DTT and alkylated with iodoacetamide prior to digestion. All bands were digested in-gel using trypsin, by adding 5 μL (10 ng/μL) trypsin in 50 mM ammonium bicarbonate and incubating overnight at room temperature to achieve complete digestion. The peptides that were formed were extracted from the polyacrylamide in two aliquots of 30 μL 50% acetonitrile with 5% formic acid. These extracts were combined and evaporated to <10 μL in a Speedvac and then resuspended in 1% acetic acid to make up a final volume of ~30 μL for LC-MS analysis.

The LC-MS system was a LTQ-Obitrap Elite hybrid mass spectrometer system (Thermo Fisher Scientific). The HPLC column was a Dionex 15 cm×75 μm id Acclaim Pepmap C18, 2 μm, 100 Å reversed-phase capillary chromatography column. 5 μL volumes of the extract were injected and the peptides eluted from the column with an acetonitrile/0.1% formic acid gradient at a flow rate of 0.25 μL/min introduced into the source of the mass spectrometer on-line. The microelectrospray ion source was operated at 2.5 kV. The digest was analyzed using the data-dependent multitask capability of the instrument, acquiring full-scan mass spectra in the Orbitrap at a resolution of 60,000 to determine peptide molecular weights and product ion spectra in the ion trap in order to determine the amino acid sequence in successive instrument scans. The data were analyzed by using all CID spectra collected in the experiment to search the human reference sequence database (March 2015 with 99,739 entries) with the search programs Mascot (version 2.3.0) and SEQUEST (version 2.2). The data were uploaded into the program Scaffold (version 4.0) for protein and peptide validation. The protein identified by at least 5 CID spectra (spectral counts) were setup as a threshold and the proteins identified in MALAT1 pull-down/control pull-down more than 2.5 were filtered as MALAT1 binding proteins for further analysis.

For MALAT1 RNA pull-down protein verification, $2\times10^7$ MM.1S or H929 cells were treated follow the same procedure described for RAP. Immunoblotting was used to verify the PARP1 and LIG3 that was pulled down by MALAT1 probe.

Immunofluorescence

MM.1S, H929 or RPMI8226 cells were rinsed in ice-cold PBS and then suspended in PBS at a concentration of $1\times10^6$ cells/mL. 100 μL cells were loaded in cuvettes and then spun onto slides at 250 g for 5 min. The cells were fixed by 4% formaldehyde at room temperature for 10 min and then permeabilized on ice for 10 min (PBS, 0.5% Triton-X100). After incubation with blocking buffer (PBS, 0.1% Tween 20, 1% BSA) for 30 min, the cells were incubated with diluted primary antibody listed as following overnight at 4° C. Rabbit anti-phosphor-histone H2A.X (Ser139) polyclonal antibody (Cell Signaling, #2577), rabbit anti-PARP1 monoclonal antibody (Cell Signaling, #9532), mouse anti-DNA ligase III monoclonal antibody (Santa Cruz Biotechnology Inc., sc-56089), rabbit anti-MRE11 monoclonal antibody (Cell Signaling, #4847), rabbit anti-NB S1 monoclonal antibody (Cell Signaling, #14956), mouse anti-XRCCS monoclonal antibody (Abcam, ab119935) or goat anti-XRCC6 polyclonal antibody (Santa Cruz Biotechnology Inc, sc-1487). Cells were washed three times by wash buffer (PBS, 0.1% Tween-20), and then incubated with diluted Alexa Fluor 647-labeled rabbit secondary antibody (Abcam), FITC-labeled mouse secondary antibody (Santa Cruz Biotechnology) or Alexa Fluor 488-labled goat secondary antibody at 37° C. for 1 hour. After 3 washes in washing buffer, cells were covered with 20 μL antifade reagent with DAPI (Vector Laboratories, Inc.) and sealed with cover slips using mounting medium. Images were captured by confocal microscopy (Leica TCS SP8) at 630× magnification.

Functionalization of Single wall Carbon Nanotube (SWCNT)

1 mg SWCNTs (#704113, Sigma) was mixed with 10 mg PL-PEG2000-NH$_2$ (Avanti Polar Lipids, 880128P) in 5 ml double-distilled water in a glass scintillation vial. The vial was sonicated in a bath sonicator (97043-992, VWR) for 1h at room temperature with water changes every 20 min to avoid overheating. The SWCNT suspension was centrifuged at 24,000 g for 6 h at room temperature and the supernatant collected. The SWCNT supernatant, 1 mL, was washed 5 times, by adding 1 mL SWCNT supernatant to a 4 mL centrifugal filter (Amicon; MilliporeSigma, UFC910008) and 33 mL double-distilled water, and centrifuging for 10 min, 4,000 g, room temperature. After the final wash, the SWCNT solution concentration was measured using a UV/VIS spectrometer (Thermo Fisher Scientific, accuSkan GO UV/Vis Microplate Spectrophotometer) with an extinction coefficient of 0.0465 L/mg/cm at 808 nm. The SWCNT concentration was adjusted to ~50 mg/L by adding the required amount of double distilled water.

Conjugation of Anti-MALAT1-1/2 Gapmer DNA Flanked by Blocks of 2'-O Modified DNAs Conjugated to SWCNTs Through Cleavable Disulfide Bond Functionalized SWCNTs, 500 µL, were mixed with 0.5 mg of Sulfo-LC-SPDP (c1118, ProteoChem). 50 µL of 10×PBS was added and incubated for 2 hours at room temperature. After incubation, the SWCNT solution was washed 5-6 times using a centrifugal filter (Amicon) by adding 3-4 mL DNase/RNase-free water and centrifuging for 6-8 min at 10,000 g each time. 15 µL anti-MALAT1(100 µM) was mixed with 1.5 µL DTT solution (Sigma, #43815), incubated for 1.5 hours at room temperature, and then DTT treated anti-MALAT1 was purified using a NAP-5 column (GE Healthcare, 17-0853-01) following the manufacturer's protocol. 500 µL anti-MALAT1 was eluted and collected from the column with DNase/RNase free 1×PBS. The activated SWCNTs were suspended with the 500 µL purified anti-MALAT1 solution and the conjugation was allowed to proceed for 24 h at 4° C.

Gapmer Anti-MALAT1 #1/#2 Oligo Flanked by Blocks of 2'-O Modified DNAs

Anti-MALAT1 #1 and #2 were synthesized by IDT Company. The sequence of anti-MALAT1 #1 was:

```
                                       (SEQ ID NO: 11)
5'-mC*mG*mA*mA*mA*C*A*T*T*G*G*C*A*C*A*mC*mA*mG*
mC*mA-3'.
```

The sequence of anti-MALAT1 #2 was:

```
                                       (SEQ ID NO: 12)
5'-mG*mG*mC*mA*mU*A*T*G*C*A*G*A*T*A*A*mU*mG*mU*
mU*mC-3'.
```

The scrambled sequence (negative control) for 2'-O-Me modified DNA was:

```
                                       (SEQ ID NO: 13)
(5'-mA*mA*mG*mG*mC*A*A*G*C*U*G*A*C*C*C*mU*mG*mA*
mA*mG-3'
m = 2'OMe; '*' = phosphorothioate (PS)linkage
```

MM Cell Apoptosis Assay

After transfection of cells with anti-MALAT1 #1 or #2 and control, apoptosis was evaluated by assaying for annexin V. Cells were stained with APC Annexin V Apoptosis Detection Kit with PI (BioLegend), according to the manufacturer's instructions. Stained cells were analyzed using flow cytometry, and data were analyzed using Flowjo software (Ashland).

MM Mouse Xenograft Anti-MALAT1-SWCNT In Situ Injection

A total of $5×10^6$ MM.1S -Luc-GFP or H929-Luc-mCherry cells in 100 µL PBS together with an equal volume of matrigel basement membrane matrix were subcutaneously injected into the shoulder to establish a human MM xenograft model with female SCID beige mice and were randomized to separate to control and treatment groups. At 14 days after tumor cell injection, 50 µL anti-MALAT1 or control oligo, which was conjugated with SWCNT (SWCNT and anti-MALAT1/ctrl concentrations are ~40 mg/L and ~2.5 µM), was injected directly into the tumor at days 14, 21, 24 and 28 after tumor cell injection blindly by a technician. Tumor development was monitored weekly using IVIS, and the mice were sacrificed at day 30. Tumor samples were subjected to RNA extraction, protein extraction, and paraffin embedding followed by in situ hybridization and immunohistochemistry analysis.

Human CD138+ Cells Isolation.

The human CD138+cells were isolated from fresh bone marrow samples of MM patients and normal bone marrow donors with CD138 Microbeads (Miltenyi Biotec).

Cell Proliferation Assay

MM cell lines (MM.1S, H929 and RPMI8226) and drug resistant MM cell lines (RPMI8226/LR5, RPMI8226/DOX40 and RPMI8226/V10R) were treated with anti-MALAT1 oligos for 24 hours. $2×10^4$ cells/well were seeded in a 96-well plate with 100 µL medium containing gradient concentration of bortezomib, melphalan or doxorubicin per well. After 72 hours culture, cells were subjected to cell viability assay using CellTilter 96® Aqueous One Solution Cell Proliferation Assay (Promega Corporation), according to the manufacturer's instructions. The half maximal inhibitory concentration (IC50) was calculated by Graphpad Prism V5.0.

Delivery of SWCNT-Anti-MALAT1 in a Disseminated MM Mouse Model 8 weeks old female NOD.CB17-Prkdcscid/J mice (Charles River lab) were used to establish mouse disseminated model of human MM. All mice were irradiated and then intravenously injected with $5×10^6$ MM.1S-Luc-GFP or $8×10^5$ H929-Luc-mCherry cells and were randomized to separate to control and treatment groups. Mice were subsequently injected with 100 uL (40 mg/mL) single-wall carbon nanotubes (SWCNT)-anti-MALAT1 or SWCNT-ctrl through the tail veins blindly by a technician, then observed daily and sacrificed once mice had paralysis. Images were acquired using an in vivo imaging system (IVIS) (PerkinElmer). Hind limb paralysis and tumor burden (diameter>2 cm) were used as end points in this disseminated disease model.

Statistical Analysis

The Student's t test was used to compare differences between the treated group and relevant control group after the variance similar between the groups was statistically compared. Overall survivals of mice with MM.1S or H929 xenografts were measured using the Kaplan-Meier method, with Cox proportional hazard regression analysis for group comparison. 5-7 mice for each group were used in animal studies based on power of 0.80 and a value of P≤0.05 was considered significant. All experiments involving animals were pre-approved by the Cleveland Clinic IACUC(Institutional Animal Care and Use Committee).

Results

MALAT1 is the Most Highly Expressed lncRNA in MGUS and MM

Figure 9A:
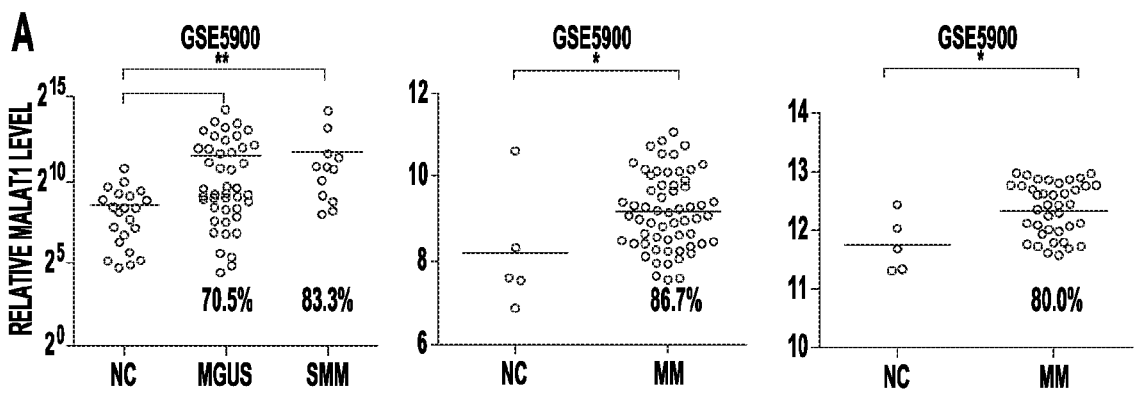
FIGS. 9A-9C provide graphs and images showing MALAT1 overexpressed in MM patients. (A) Relative MALAT1 expression levels in 3 published microarray datasets (*p<0.05, **p<0.01). (B) Representative images of ISH and immunohistochemical staining showing MALAT1 expression and CD138+ cells within bone marrow of the patients and controls (scale bar=100 µM). The relative density of MALAT1 or CD138 signal was quantified by Image J, and summarized in the histogram. (C) Relative MALAT1 levels in 5 MM cells lines and plasma cells separated from 7 MMs and 4 HDs.

We first analyzed gene expression microarray datasets uploaded by 3 different groups, including Zhan dataset (GSE5900) (Zhan et al., Blood, 109(4): 1692-1700 (2007)), Gutierrez dataset (GSE16558)(Gutierrez et al., Leukemia, 629-637 (2010)) and Lopez-Corral dataset (GSE47552) (Lopez-Corral et al., Haematologica, 99(8): 1365-1372 (2014)). Analysis of all 3 datasets showed that MALAT1 expression was higher in MGUS, SMM and MM compare with healthy donors (HDs, FIG. 9A).

Figure 9B:
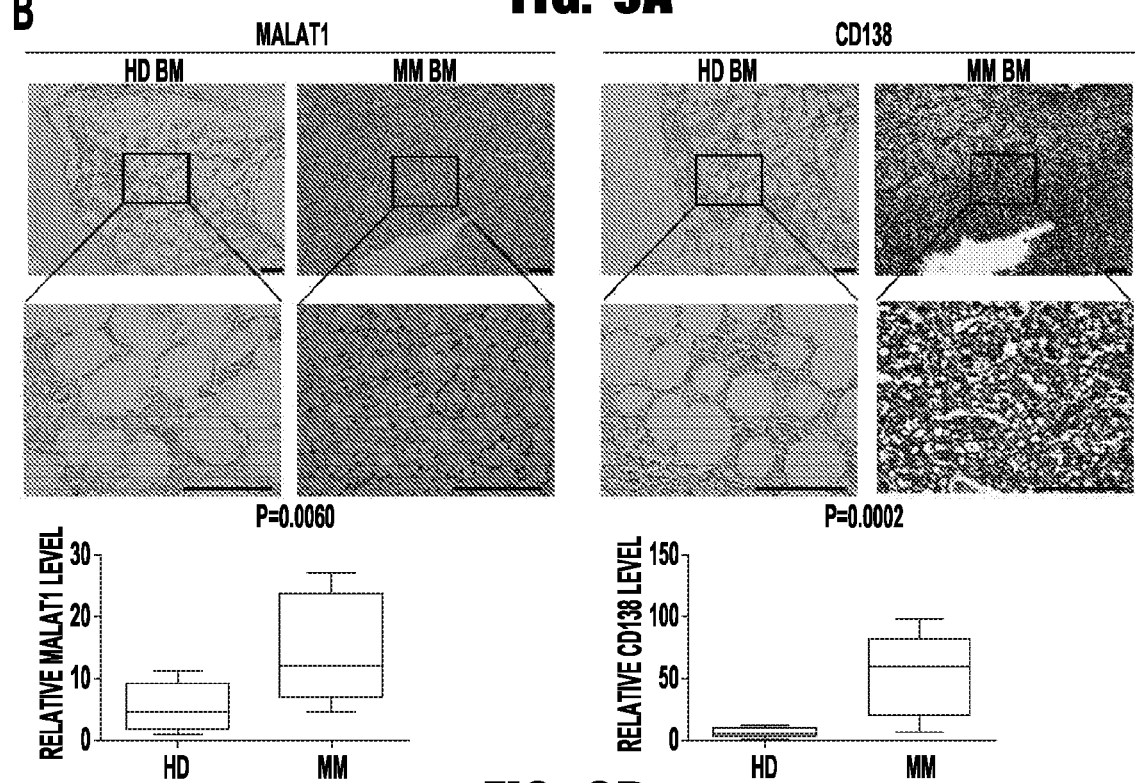
Figure 9C:
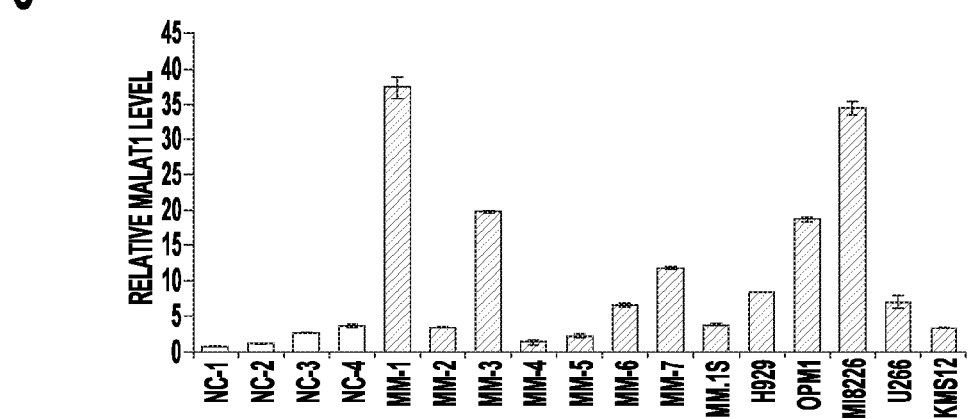

We next used in situ hybridization (ISH, FIG. 9B) and qRT-PCR (FIG. 9C) to detect MALAT1 in clinical MM samples and cell lines, and verified that MALAT1 was highly expressed in BM CD138+ cells from MM patients compared with HDs, which was consistent with microarray data. Furthermore, two groups have reported that MALAT1 overexpression was significantly correlated to poor prognosis in MM patients, including shorter progression-free survival (PFS) and overall survival (OS). Handa et al., Br J Haematol, 179(3):449-460 (2017)

MALAT1 Over-Expression Accelerated Proliferation and Repressed Apoptosis in MM

To explore the functions of over-expressed MALAT1 in MM, we infected V-MALAT1 or V-ctrl into MM.1S cells, and added puromycin for selection, then injected subcutaneously to the shoulders of SCID mice (FIG. 1A). Diameters of tumor were measured once a week, the growth of MM.1S-V-MALAT1 xenografts was significantly faster than controls (FIG. 1A). MALAT1 levels in MM.1S-V-MALAT1 xenografts were over-expressed confirmed by qRT-PCR (FIG. 1B). MM.1S-V-MALAT1 xenografts compared with the MM.1S-V-ctrl xenografts have higher proliferation and less apoptosis according to immunohistochemistry staining of Ki-67 and c-caspase3 (FIG. 1C).

MALAT1 Binds with PARP1/LIG3 Complex in MM

Figure 10A:
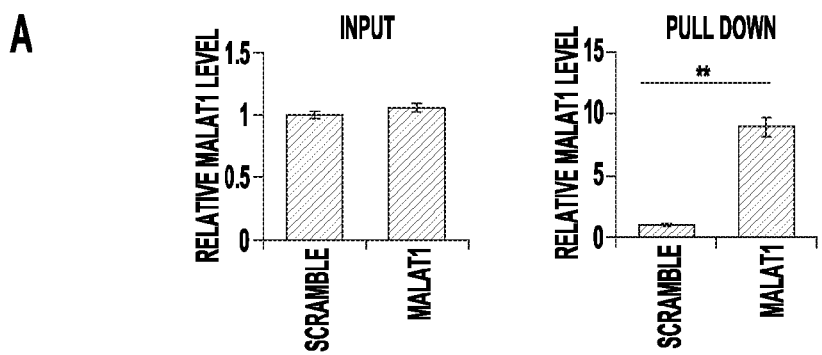
FIGS. 10A-10C provide graphs and images showing MALAT1 binding protein identification. (A) qRT-PCR showed MALAT1 was enriched by probe (**p<0.01). (B) Identification of the MALAT1 binding proteins. After staining, two specific band clusters were found in the MALAT1 pull-down sample. MS results indicated that the 98 kD cluster contained PARP1 and LIG3, and the cluster between 14 kD and 17 kD was identified as SUB1 and RBM3. (C) STRING database analysis of MALAT1 pull-down proteins.
Figure 10B:
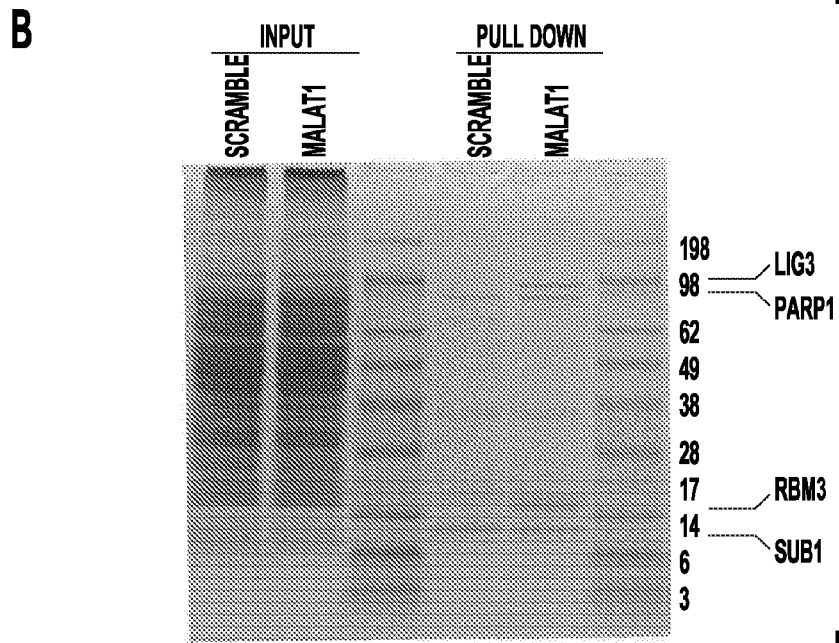
Figure 10C:
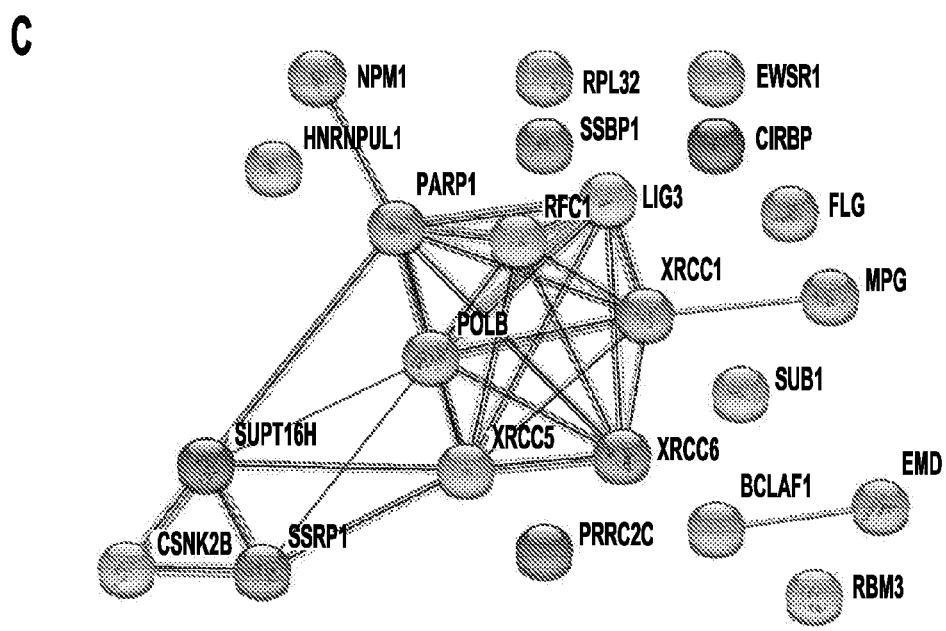

To investigate the co-factors binding to MALAT1 in MM cells, we used RNA antisense purification-mass spectrum (RAP-MS) to identify MALAT1 binding proteins (FIG. 2A). Biotin-labeled anti-MALAT1 DNA probe was used to pull-down MALAT1 in H929 cells, then MALAT1 pull-down sample was used to run a PAGE gel and subjected to MS analysis. (FIG. 10A-B). Using RAP-MS whole proteomic analysis, we identified 23 MALAT1 binding proteins (Table 1). STRING database functional enrichment analysis revealed 10 of these proteins were related to DNA repair pathways (GO:0006281, false discovery rate 9.89e-08), including PARP1, LIG3, XRCC1, XRCC5, XRCC6, SUPT16H, NPM1, RFC1, SSRP1 and MPG (FIG. 10C). The notable proteins with strong signals, including PARP1, LIG3, and XRCC5 were further verified by western blot using MALAT1 pull-down protein lysate from H929, MM.1S and RPMI8226 cells, respectively (FIG. 2B). The co-localization between MALAT1 and PARP1 was further confirmed by immunofluorescence staining. As shown in FIG. 2C, more than 70% of the PARP1 signal was co-localized with MALAT1 signal in H929, MM.1S, and RPMI8226 cells.

TABLE 1

MALAT1 binding proteins identified by mass spectrometry

| Gene name | Molecular weight (kD) | Spectral Counts Con | Pull-down | Folds (Pull-down/Con) |
|---|---|---|---|---|
| BCLAF1 | 100 | 1 | 6 | 6 |
| CIRBP | 19 | 2 | 9 | 4.5 |
| CSNK2B | 25 | 4 | 13 | 3.25 |
| EMD | 29 | 2 | 6 | 3 |
| EWSR1 | 68 | 2 | 6 | 3 |
| FLG | 430 | 1 | 8 | 8 |
| HNRNPUL1 | 86 | 1 | 5 | 5 |
| LIG3 | 114 | 0 | 32 | Pull-down only |
| MPG | 33 | 0 | 13 | Pull-down only |
| NPM1 | 33 | 1 | 6 | 6 |
| PARP1 | 113 | 92 | 309 | 3.36 |
| POLB | 38 | 0 | 8 | Pull-down only |
| PRRC2C | 309 | 1 | 14 | 14 |
| RBM3 | 17 | 0 | 5 | Pull-down only |
| RFC1 | 128 | 2 | 7 | 3.5 |
| RPL32 | 16 | 1 | 6 | 6 |
| SSBP1 | 16 | 2 | 11 | 5.5 |
| SSRP1 | 81 | 1 | 6 | 6 |
| SUB1 | 14 | 19 | 167 | 8.79 |
| SUPT16H | 120 | 1 | 21 | 21 |

TABLE 1-continued

MALAT1 binding proteins identified by mass spectrometry

| Gene name | Molecular weight (kD) | Spectral Counts | | Folds (Pull-down/Con) |
|---|---|---|---|---|
| | | Con | Pull-down | |
| XRCC1 | 70 | 3 | 21 | 7 |
| XRCC5 | 83 | 2 | 12 | 6 |
| XRCC6 | 70 | 2 | 8 | 4 |

PARP1 was intensively investigated multiplefunctional protein which has been implicated in recognition of DNA single and double strand break (SSB and DSB)s during DNA repair and catalyzes PAR formation to induce cell apoptosis. Huambachano et al., The Journal of biological chemistry, 286(9): 7149-7160 (2011). According to our RAP-MS results, MALAT1 pulled down PARP1, as well as other DNA repair proteins, thus we hypothesized that MALAT1 acts as a scaffold, to form functional complexes through bundling PARP1 and other proteins, then exerted its function in DNA repair pathway(s). To validate this hypothesis, we firstly used ribonucleoprotein immunoprecipitation (RIP) strategy to further prove the binding between MALAT1 and PARP1 in myeloma cells. As shown in FIG. 3A, the RNA-protein complexes in myeloma cells were first cross-linked by UV, then the cell lysate was incubated with PARP1 antibody-coated magnetic beads. After washing, total RNA was extracted from the precipitate, then the MALAT1 level was determined by qRT-PCR. We found PARP1 antibody-coated beads specifically enriched PARP1 signal (FIG. 3B), and MALAT1 was also enriched by PARP1 antibody-conjugated beads exclusively (FIG. 3C), which demonstrated direct interaction between MALAT1 and PARP1. Although there no RNA binding domain on LIG3, poly(ADP-ribose) polymerase and DNA-Ligase Zn-finger (zf-PARP) regions are present that can bind PARP1 (Leppard et al., Mol Cell Biol, 23(16): 5919-5927 (2003)). PARP1 and LIG3 are critical molecules involved in the A-NHEJ DNA repair pathway. Chiruvella et al., Cold Spring Harb Perspect Biol, 5(5): a012757 (2013) Thus, we postulated that MALAT1 might play its role in A-NHEJ DNA repair by direct binding with PARP1 and indirect binding with LIG3.

MALAT1 Inhibition Induced DNA Damage and Apoptosis in MM

To demonstrate our postulation, we used two gapmer DNA antisense oligos targeting MALAT1(anti-MALAT1-1/2) to knock-down MALAT1 expression and perform loss-of-function study of MALAT1 in MM cells. The gapmer DNA was flanked by blocks of 2'-OMe-modified RNAs, which would bind to MALAT1 RNA and induce cleavage of MALAT1 by RNase H. Lennox et al., Nucleic acids research, 44(2): 863-877 (2016). qRT-PCR analysis showed MALAT1 was efficiently knocked-down in H929 (FIG. 4A), MM.1S (FIG. 4B) and RPMI8226 cells (FIG. 4C). The frequency of DNA break increased substantially as revealed by immunofluorescence staining and western blot for γH2A.X. Interestingly, we found that PAR signal increased after MALAT1 knock-down indicating that MALAT1 antagonist did not inhibit, but enhanced PARP1 catalytic activity by releasing PARP1 from MALAT1/PARP1 complex, which would induce cell apoptosis directly. Simbulan-Rosenthal et al., J Biol Chem, 273(22): 13703-13712 (1998) Furthermore, defective DNA repair induced more cleavage of PARP1 and caspase3 (c-PARP1 and c-caspase3), which also contributed to cell apoptosis in MM cells. We also observed significantly increased apoptosis by flow cytometry analysis after anti-MALAT1 treatment (FIG. 4A-C).

Figure 11:
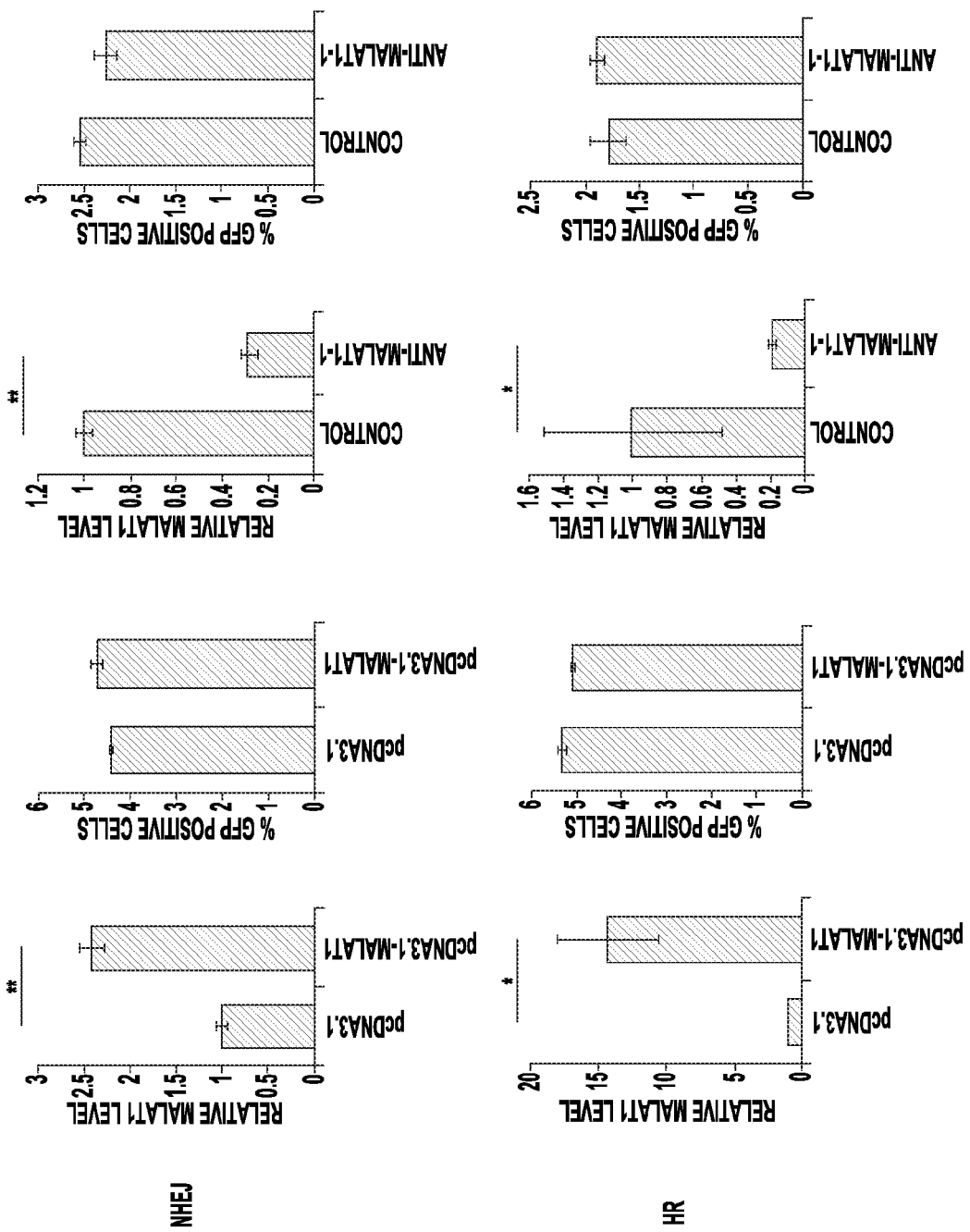
FIG. 11 provides graphs showing that MALAT1 did not regulate NHEJ and HR pathways. In NHEJ (pimEJ5GFP) and HR (pDRGFP) reporter plasmid stable transfected HEK293T cells, pCBA-Scel was transient transfected with and MALAT1 overexpression/empty vectors or anti-MALAT1/control gapmer. The number of GFP positive cells was determined by flow cytometry and the MALAT1 level was detected by qRT-PCR. (*p<0.05, **p<0.01)
Figure 12A:
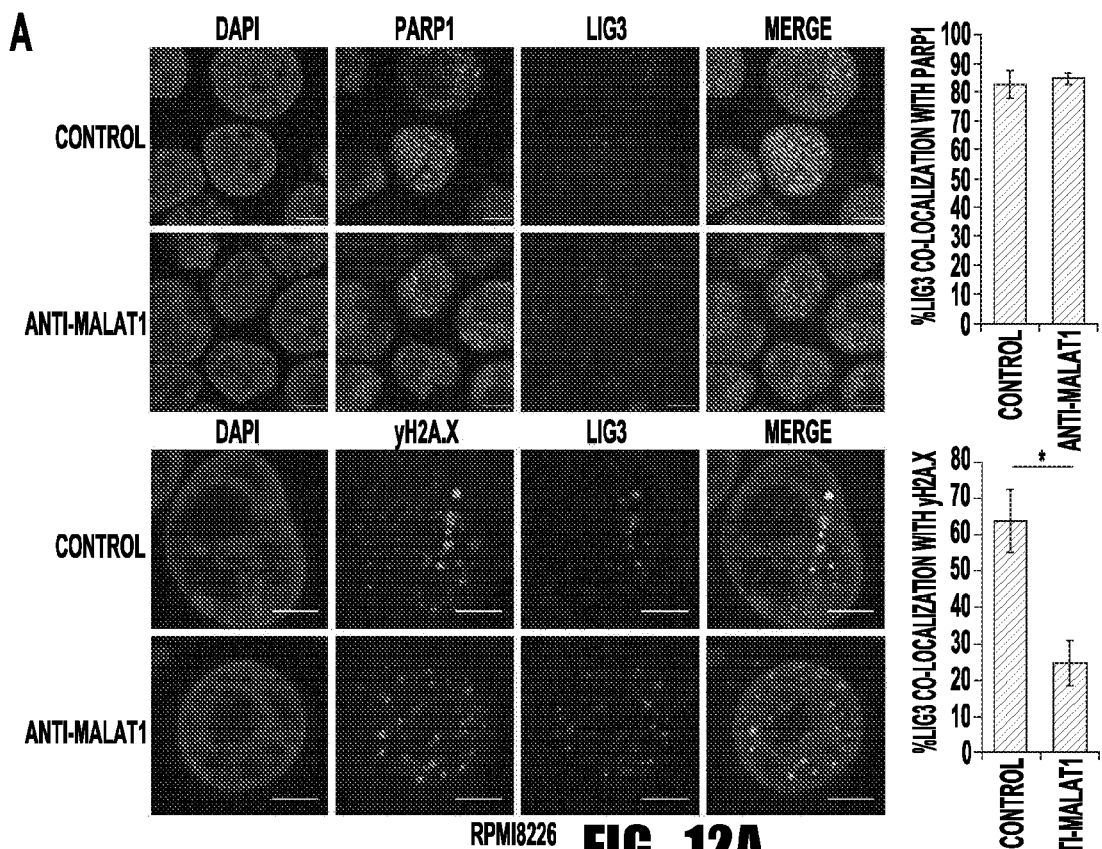
FIGS. 12A and 12B provide images and graphs showing that MALAT1 is required for LIG3 recruitment on DSB loci. The co-localization between PARP1 and LIG3, or γH2A.X and LIG3 before and after MALAT1 knockdown were determined by immunofluorescence staining (scale bar=2.5 µM) in RPMI8226 (A) and MM.1S (B) cells. (*p<0.05)
Figure 12B:
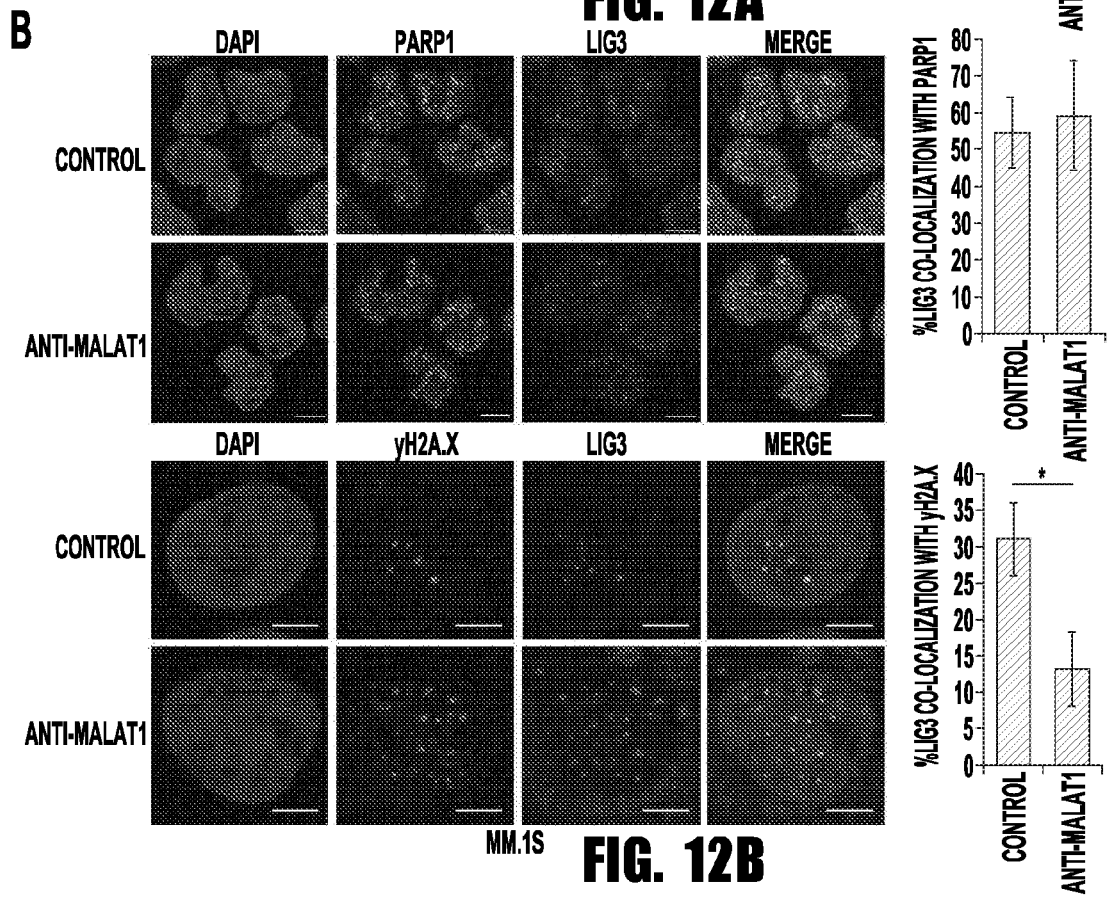

To determine whether MALAT1 specifically involved in A-NHEJ DNA repair pathway, we generated pEJ2GFP-puro (A-NHEJ reporter), pimEJ5GFP(NHEJ reporter) and pDRGFP(HR reporter) stable cell lines in HEK293T cells separately. I-SceI was used to generate DNA damages at I-SceI sites on these plasmids. MALAT1 overexpression vector or anti-MALAT1 gapmer DNA were used to up-/down-regulate the expression of MALAT1. All vectors would produce GFP once the plasmid DNAs were repaired by correspondent functions, thus we could evaluate which DNA repair pathway involved by examining GFP positive ratio by flow cytometry. As shown in FIG. 5A, HEK293T-EJ2GFP with over-expressed MALAT1 had significant increase of GFP positive cells, whereas HEK293T-EJ2GFP with knocked-down MALAT1 had significant decrease of GFP positive cells. However, no significant difference was found in the HEK293T-imEJ5GFP and HEK293T-DRGFP cells with up-/down-regulation of MALAT1 (FIG. 11), indicating that MALAT1 specifically involved in A-NHEJ pathway. The result were further verified by immuofluoresence staining of LIG3/PARP1 and LIG3/γH2A.X in H929 cells after we knocked down MALAT1. We found MALAT1 knock-down had no influence on LIG3/PARP1 co-localization (FIG. 5B, FIG. 12), but interrupted the co-localization between LIG3 and γH2A.X (FIG. 5C, FIG. 12). These results demonstrated that MALAT1 is crucial in A-NHEJ pathway through recruiting LIG3 to γH2A.X loci on DSB.

Figure 13A:
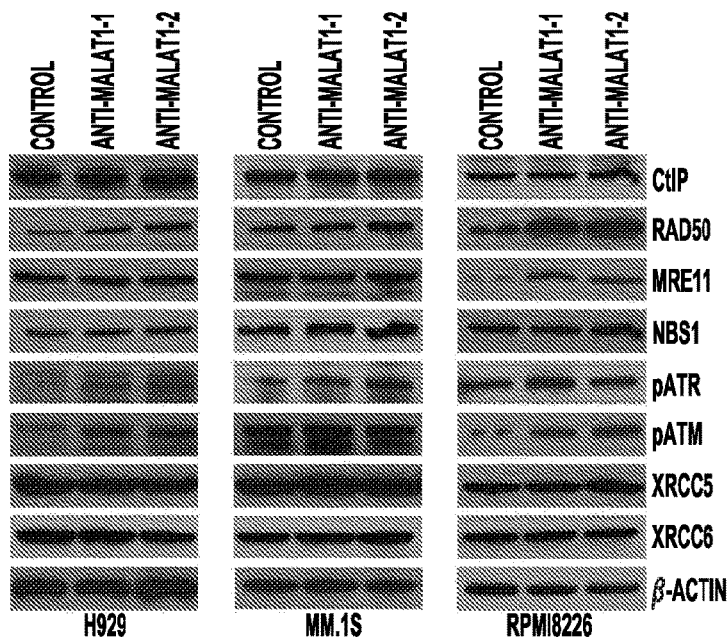
FIGS. 13A-13C provide graphs and images showing MALAT1 knock down didn't influence the MRN complex and XRCC5/XRCC6 complex formation. (A) 2'-OMe-modified anti-MALAT1 oligos or control oligos were transfected into H929, MM.1S or RPMI8226 cells, respectively. At 48 h after transfection, cells were collected and subjected to immunoblotting of CtIP, RAD50, MRE11, NBS1, pATM, pATR, XRCC5, XRCC6 and β-actin. The co-localization between MRE11 and NBS1 (B) or XRCC5 and XRCC6 (C) were determined by immunofluorescence staining (scale bar=5 µM) in H929, MM.1S and RPMI8226 cells transfected with anti-MALAT1 or control.
Figure 13B:
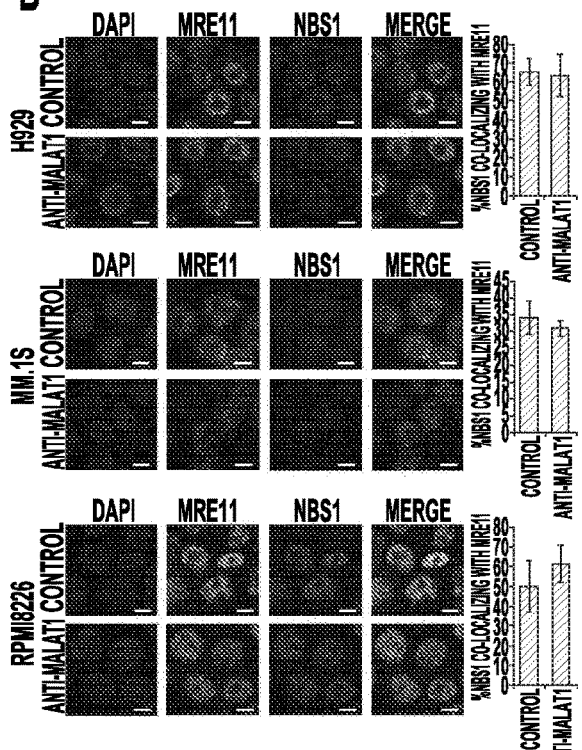
Figure 13C:
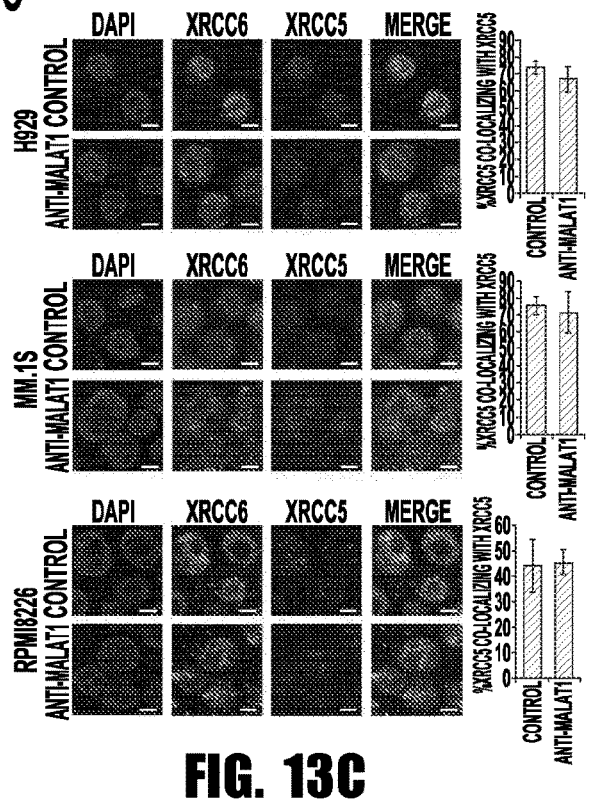

To further understand how does MALAT1 knock down affect other components of A-NHEJ DNA repair pathway, NHEJ pathway, and HR pathway, we detected the expression levels of proteins involved in these pathways including CtIP, MRE11, RAD50, NBS1, p-ATM, p-ATR, XRCC5 and XRCC6. We found that RAD50, pATM, or pATR upregulated in all three MM cell lines, MRE 11 upregulated in RPMI8226 cell line, after MALAT1 was knockdown, but not CtIP, NBS1, XRCC5 and XRCC6 protein levels (FIG. 13A). To determine if MALAT1 inhibition will affect MRE11-RAD50-NBS1 (MRN) complex or XRCC5 and XRCC6 complex formation, we did immunoflurecence staining of MRE11 and NBS1, XRCC5 /XRCC6 complex in MM cell lines. We found that MALAT1 knock down didn't influence the MRN complex and XRCC5/XRCC6 complex formation (FIG. 13B-C), indicating MALAT1 is dispensable for the initial DSB recognition of either A-NHEJ or NHEJ or HR pathways.

PARP1 Inhibitor Cooperated with MALAT1 Antagonist to Induce DNA Damage and Apoptosis in MM To determine whether inhibiting the dissociated PARP1 catalytic activity induces additional DNA damage to further increase cell death after anti-MALAT1 treatment in MM cells, we used the PARP1 inhibitor ABT888 to specially inhibit PARP1 activity in MALAT1 knocked-down MM cells. We observed increased PAR signal in H929 and MM.1S when treated with anti-MALAT1 only, but saw dose-dependent decreased PAR signal in the same cell lines treated synchronously with anti-MALAT1 and ABT888. Combination treatment significantly increased the level of γH2A.X, cleaved PARP1, and cleaved caspase-3 (FIG. 5C).

MALAT1 Inhibition Potentiates the Cytotoxic Effects of Bortezomib in MM

Bortezomib treatment could induce "BRCAness" in MM and impair HR pathway. Neri et al., Blood, 118(24): 6368-6379 (2011). Our results have demonstrated that repressing MALAT1 inhibited A-NHEJ activity, thus we postulated that MALAT1 antagonists might have synergistic effect with bortezomib by disabling both HR and A-NHEJ pathways, then provoked cell death by inducing severe DNA damages in MM. To verify our assumption, anti-MALAT1-1 or scrambled DNA oligos was transfected into H929, MM.1S and RPMI8226 cells and treated with various doses of bortezomib, then cells were collected for apoptosis assay. We found expression of BRCA1 and BRCA2 were dramatically down-regulated in all 3 cell lines received high-dose bortezomib treatment (FIG. 6A-C). Whereas γH2A.X signals and apoptosis ratio were increased by both high-/low-dose bortezomib treatment, and these effects were amplified by combining with anti-MALAT1 treatment. Meanwhile, anti-MALAT1 treated MM cells were more sensitive to bortezomib compared to untreated cells according to our cell viability assay, which showed the IC50 reduced from 4.9 nM to 3.6 nM in H929 cells, from 8.9 nM to 6.6 nM in MM.1S cells, and from 10.1 nM to 8.2 nM in sensitivity to bortezomib compared with control cells (FIG. 6A-C). These results implied that bortezomib and anti-MALAT1 acted synergistically to induce MM cell death via promoting DNA damages.

Figure 15A:
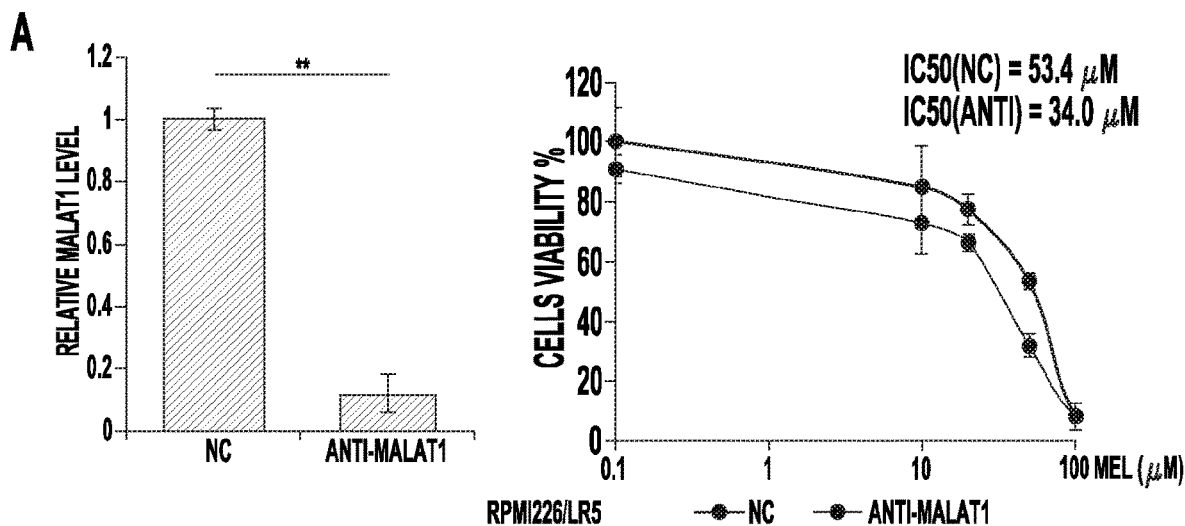
FIGS. 15A-15C provide graphs showing Anti-MALAT1 treated drug resistant MM cells become sensitive to the drugs. RPMI8226/LR5(A), RPMI8226/DOX40(B) and RPMI8226/V10R(C) cells were transfected with 1 nM anti-MALAT1 or control oligos, and treated with melphalan, doxorubicin, and bortezomib respectively. Cells were collected for cell viability assay. (*p<0.05, p<0.01, *p<0.001)
Figure 15B:
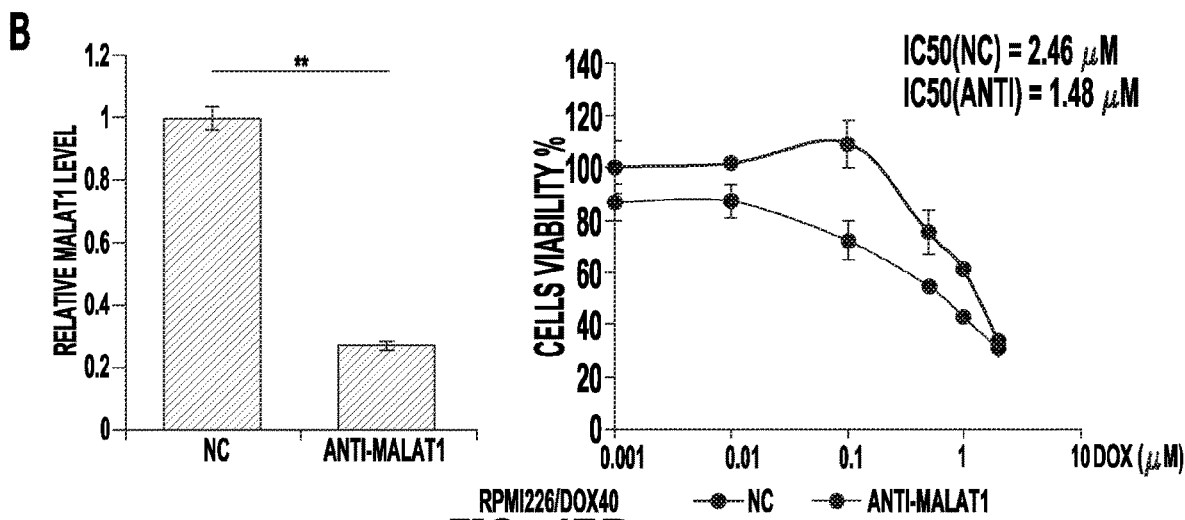
Figure 15C:
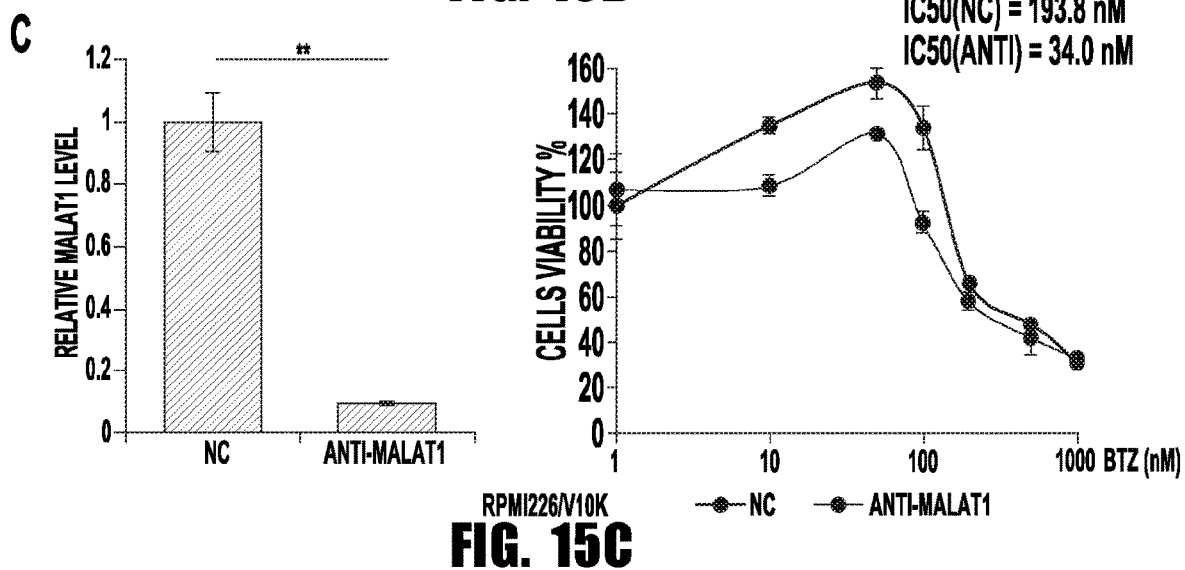

To understand the role of MALAT1 in drug resistance in MM, we used bortezomib-, melphalan- and doxorubicin-resistance MM cell lines, RPMI8226/V10R, RPMI8226/LR5 and RPMI8226/DOX40 and their parental cell line RPMI8226 used as control. We found MALAT1 expression was significantly higher in these resistant MM cell lines compared with RPMI8226 cells (FIG. 14A). Furthermore, after MALAT1 level was knocked-down (FIG. 14B), an increased apoptotic cells numbers were observed in all three resistant cell lines (FIG. 14C). IC50 of RPMI8226/LR5 cells to melphalan decreased from 53.4 µM to 34.0 µM, RPMI8226/DOX40 cells to doxorubicin decreased from 2.46 µM to 1.48 µM and RPMI8226/V10R to bortezomib decreased from 193.8 nM to 143.9 nM, respectively (FIG. 15A-C). Those results indicated that anti-MALAT1 treatment resensitized resistant MM cells to their corresponding drugs again.

Figure 7A:
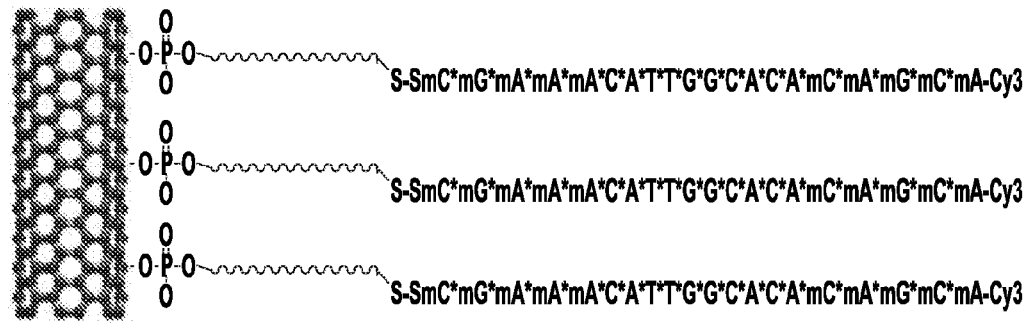
FIGS. 7A-7C provide graphs and images showing that SWCNT-anti-MALAT1 showed high delivery efficiency and minimal toxicity. (A) Schematic diagram of SWCNT-anti-MALAT1-Cy3 gapmer oligos (Scale bars=100 µM). (B) H929-GFP and MM.1S-GFP cells were co-cultured with SWCNT-anti-MALAT1-cy3 for 48 h. (C) MALAT1 level was knocked-down successfully (p<0.01, *p<0.001).
Figure 7B:
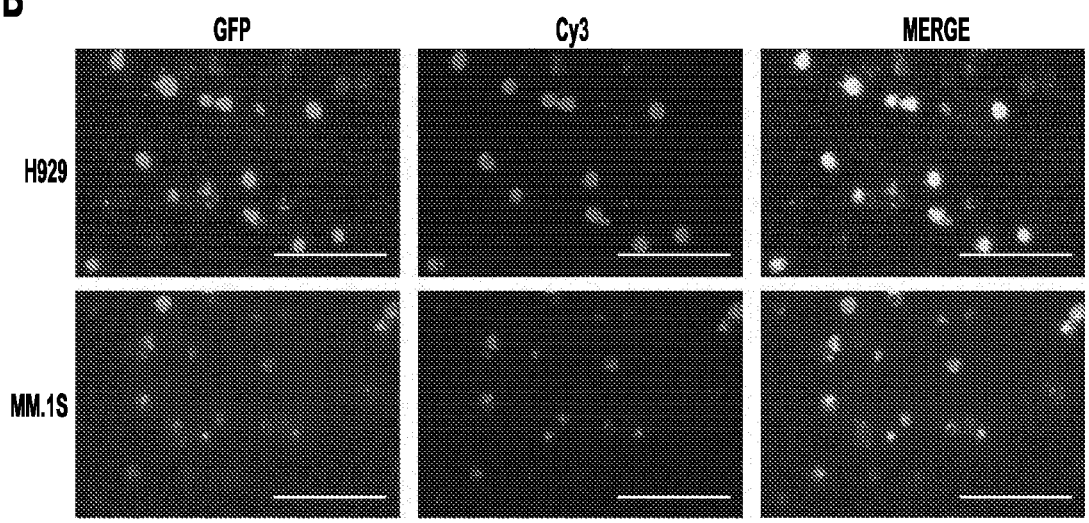
Figure 7C:
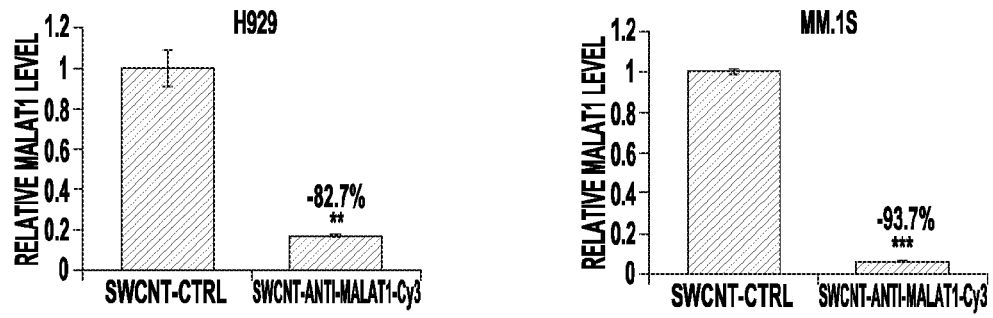

SWCNT-Anti-MALAT1 Oligo Repressed MM Proliferation and Induced Cell Apoptosis In Vivo Our data indicated that MALAT1 antagonist was a robust tool to provoke DNA damage and apoptosis in MM. However, the efficient delivery of anti-MALAT1 oligos in vivo was the main obstacle that limits clinical application of this type of therapy. As a novel nanomaterial for drug delivery, SWCNT may deliver nucleic-acid drugs stably and efficiently with good tolerability and minimal toxicity in vitro (Jiang et al., Nanoscale, 5(16): 7256-7264 (2013)) and in vivo (Murakami et al., Nanomedicine (Lond), 3(4): 453-463 (2008)). To track the delivery visible, we conjugated SWCNT with Cy3-labeled-anti-MALAT1 oligos(SWCNT-anti-MALAT1-Cy3)(FIG. 7A) (Luo et al., Hepatology, 44(4): 1012-1024 (2006)), and then added it into culture medium of H929-GFP and MM.1S-GFP cells to validate delivery efficiency. As shown in FIG. 7B, SWCNT-anti-MALAT1-Cy3 was delivered into the nucleus of MM cells efficently and suppressed the endogenous MALAT1 level in both H929 and MM.1S cells significantly (FIG. 7C).

To further estimate the treatment potential of SWCNT-anti-MALAT1 in vivo, we subcutaneously injected MM.1S-Luc-GFP cells on the back of SCID mice to establish human MM xenograft murine model (FIG. 8A). At day 14 after tumor cell injection, SWCNT-anti-MALAT1 or SWCNT-ctrl oligos were injected directly into tumors and repeated at days 21, 24 and 28, respectively. We observed tumor burden with IVIS after luciferin injection, and found the luciferin signal was significant lower in SWCNT-anti-MALAT1 treated group compared with SWCNT-ctrl treated group. Then we measured MALAT1 level with RNA samples extracted from tumor xenografts and found that MALAT1 expression was significantly downregulated by SWCNT-anti-MALAT1 treatment, which indicated SWCNT delivered MALAT1 antisense oligo efficiently into MM cells in this human MM xenograft murine model. Western-blot results showed c-PARP1 increased in anti-MALAT1 treatment group. Immunohistochemistry results revealed decreased Ki-67 and increased c-caspase3 signals on SWCNT-anti-MALAT1 treated tumor sections.

Figure 8B:
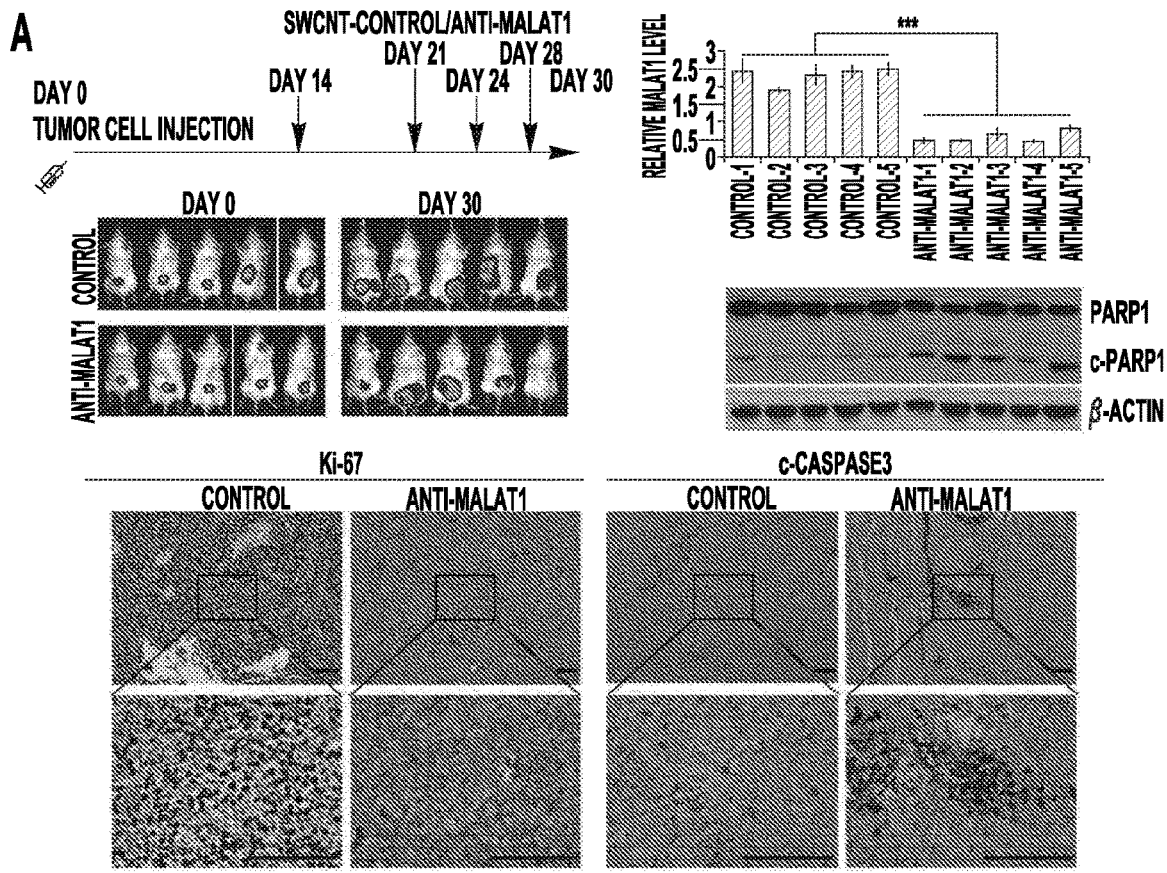
Figure 8B:
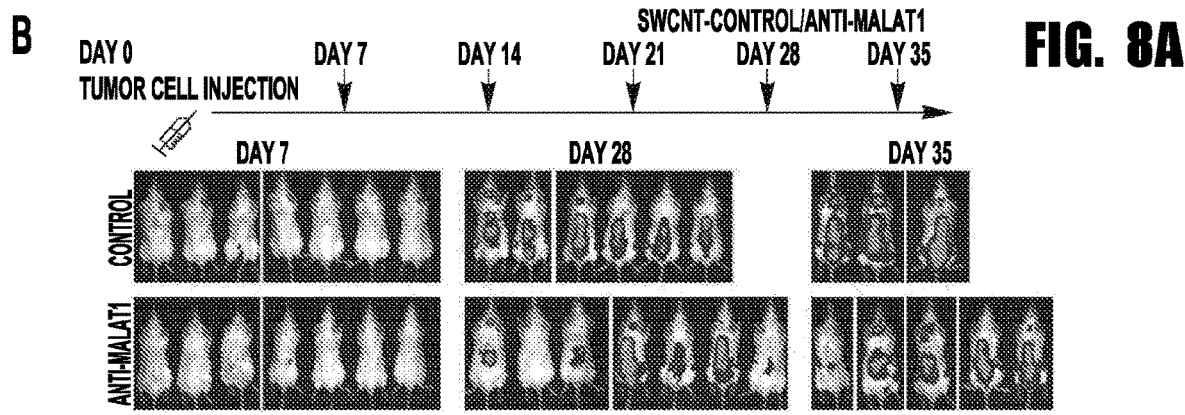
Figure 8B:
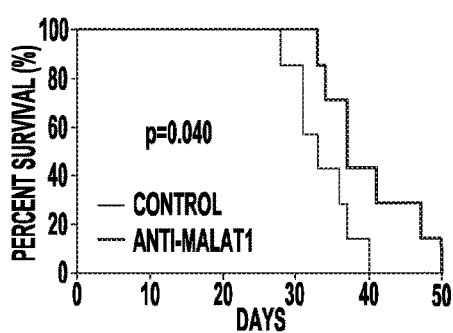

MM is a systematic disease and malignant cells usually involve multiple organs in patient. To mimic this situation, we generated a disseminated MM murine model, and used SWCNT-anti-MALAT1 to test treatment effect on it (FIG. 8B). We firstly intravenously injected MM.1S-Luc-GFP cells into SCID mice through tail veins. At day 7 after tumor cell injection, SWCNT-anti-MALAT1 or SWCNT-ctrl oligos were injected through tail veins and repeated at days 14, 21, 28 and 35, respectively. We detected luciferin signal at day 35 and recorded their survival status, then we found SWCNT-anti-MALAT1 treatment not only reduced the tumor burden, but extended lifespan significantly($P=0.04$) compare with SWCNT-ctrl treated group.

Figure 16A:
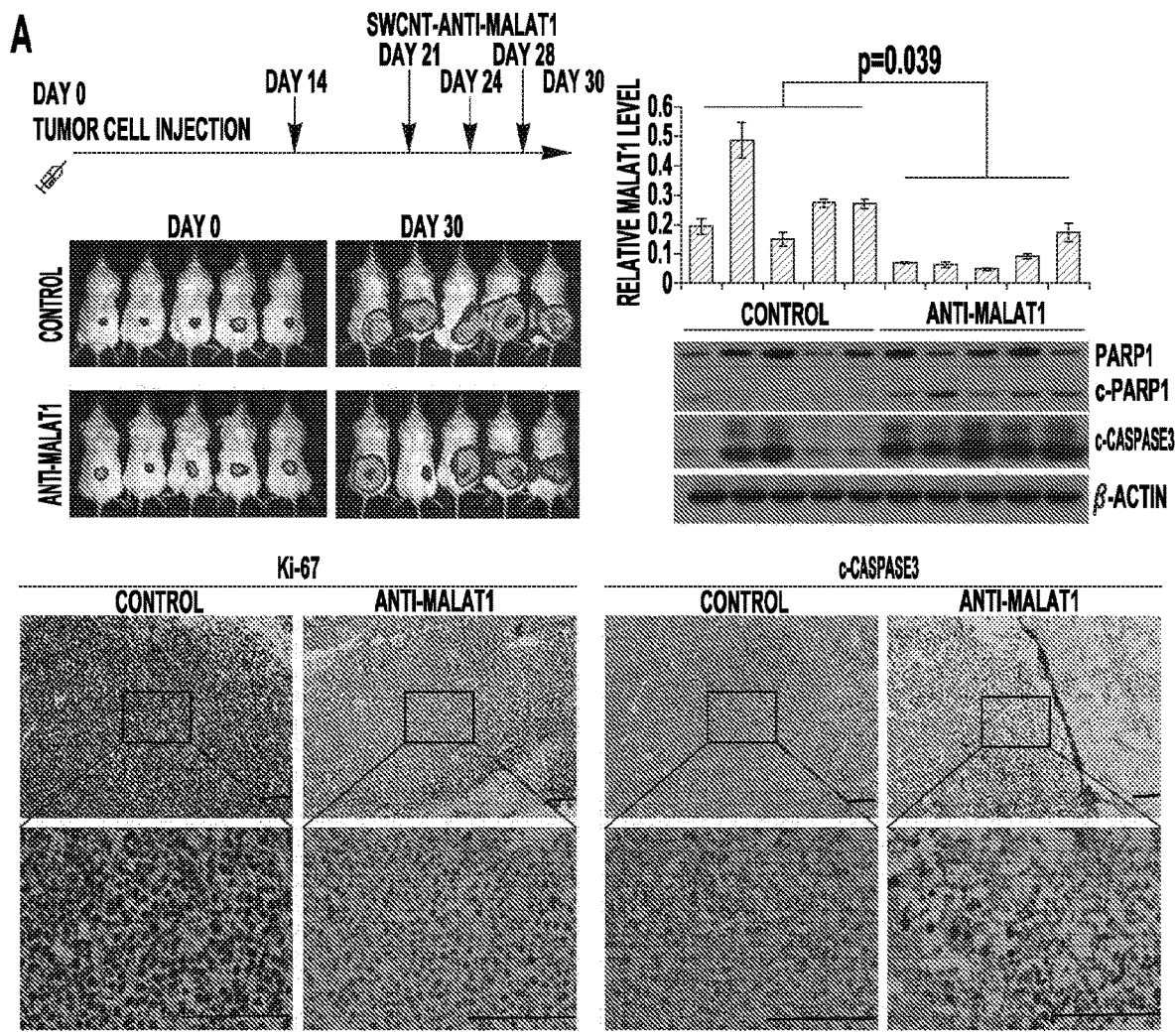
FIGS. 16A and 16B provide graphs and images showing that SWCNT-anti-MALAT1 treatment repressed myeloma growth in H929 cell constructed MM murine models. (A) $5 \times 10^6$ H929-Luc-mCherry cells were injected subcutaneously to the shoulders of SCID mice. SWCNT-anti-MALAT1 conjugates were injected into the tumors at the indicated days; with SWCNT-anti-GFP as control. Tumor growth was monitored by IVIS. Mice were sacrificed 30 days after the final injection, and the tumor samples were subjected to qRT-PCR, immunoblotting, and immunohistochemistry (Scale bars=100 µM). (B) SCID mice (5 mice each group) were irradiated and then intravenously injected with $5 \times 10^6$ H929-Luc-GFP cells. Mice were subsequently injected with 100 μL (~40 mg/mL) SWCNT-anti-MALAT1 or SWCNT-ctrl once every week through the tail veins and then observed daily and sacrificed following development of paralysis or overload tumor burden. Hind limb paralysis and tumor burden were used as end points, and the survival data were analyzed by Kaplan-Meier analysis.
Figure 16B:
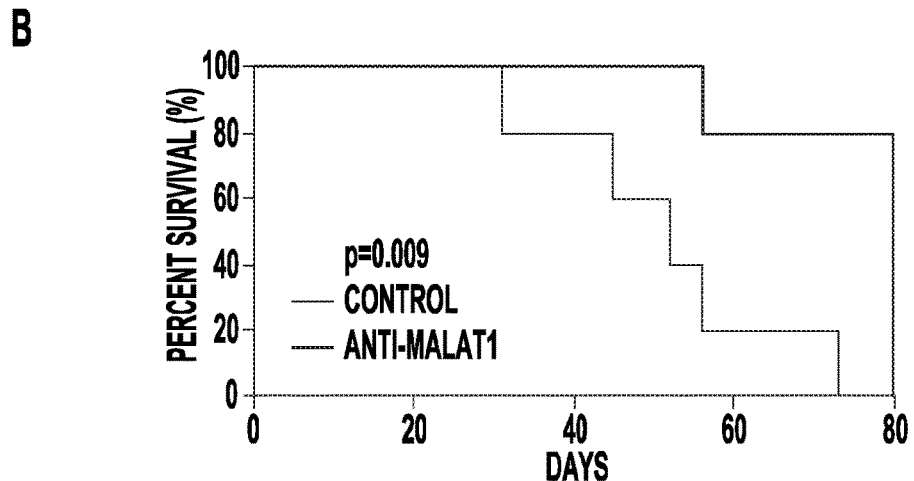

To further confirm the therapeutic effect of anti-MALAT1 in MM in vivo, we generated another murine xenograft model and disseminated model with H929-Luc-mCherry cells (FIG. 16). We found SWCNT-anti-MALAT1 inhibited H929 growth dramatically in both models. Meanwhile, SWCNT-anti-MALAT1 efficiently knocked-down MALAT1 expression, upregulated c-PARP1 and c-caspase3, and inhibited Ki-67 signal. In H929 disseminated model, SWCNT-anti-MALAT1 treatment extended mice lifespan significantly ($P=0.009$).

Discussion

This study is the first to elucidate the function of the lncRNA MALAT1 in MM. PARP1 and LIG3 are two key molecules required for the highly error-prone A-NHEJ31 DNA repair pathway. We demonstrated that MALAT1 is critical for PARP1/LIG3 complex to recognize DSBs γH2A.X loci on DNA, then activated A-NHEJ DNA repair in MM. LIG3 is upregulated in multiple myeloma (Herrero et al., PLoS One, 10(3): e0121581 (2015)), chronic myeloid leukemia (Sallmyr et al., Blood, 112(4): 1413-1423 (2008)), and breast cancer (Tobin et al. Molecular cancer research: MCR, 10(1): 96-107 (2012)). Strikingly, A-NHEJ is associated with frequent chromosome abnormalities such as deletions, translocations, inversions, and other complex rearrangements. Muvarak et al., Molecular cancer research: MCR, 13(4): 699-712 (2015). Thus over-expression of MALAT1 in MM may enhance A-NHEJ DNA repair pathway to induce secondary chromosome changes (Soni et al., Nucleic Acids Res, 42(10): 6380-6392 (2014)), which may promote disease progression, but also induce drug resistance. Dissecting the mechanism of how MALAT1 directly or indirectly recruits LIG3 to γH2A.X loci, which represents DSBs, to favor A-NHEJ repair pathway will be our next focus by investigating the function of different domains on LIG3 and PARP1. Further gain-of-function studies of MALAT1 in normal or precursor cells and transgenic mice will be needed in the future to confirm our findings.

To evaluate MALAT1 as a possible therapeutic target, we pursued antisense inhibition and observed increased DNA damage and apoptosis in MM cells due to dissociation of the MALAT1/PARP1/LIG3 complex and deregulation of A-NHEJ pathway. We verified that knock-down MALAT1 in MM cells had synergistic effect with PARP1 inhibitor or bortezomib through inducing more cell apoptosis. Most of U.S. Food and Drug Administration (FDA)-approved PARP1 inhibitors are used to inhibit the catalytic activity of PARP1 and increase DNA damage in ovarian cancer with BRCA1/2 mutations, where the HR pathway is defected. Unrepaired DNA damage will induce cell apoptosis. MALAT1 antagonist acts its role through PARP1 but the underlying mechanism is different from PARP1 inhibitors. In contrast, Anti-MALAT1 treatment disrupts MALAT1/PARP1/LIG3 DNA repair complex, then dissociated free PARP1 will induce polyADP-ribosylation in the nucleus, which will promote cell apoptosis directly. Anti-MALAT1 treatment will also impaired the A-NHEJ DNA repair pathway, which will further induce cell apoptosis due to unrepaired DSB DNA. When combined bortezomib and anti-MALAT1 therapy in MM, bortezomib repressed HR through reducing BRCA1/2 expression, meanwhile anti-MALAT1 inhibited A-NHEJ activity, thus apoptosis accumulated dramatically through synchronous dysfunction of two DSB repair pathways. These results provide new therapeutic strategy for MM patients.

To today, FDA has approved several antisense oligonucleotide drugs, including nusinersen for spinal muscular atrophy, mipomersen for homozygous familial hypercholesterolemia, fomivirsen for cytomegalovirus retinitis, and eteplirsen for Duchenne muscular dystrophy. We used gapmer DNA flanked by 2'-OMe-modified MALAT1 antisense oligonucleotides to achieve remarkable inhibition effects, and applied SWCNT as delivery system to improve affinity, stabilize the oligos and against nuclease degradation during delivery. To the best of our knowledge, this is the first report to use functionalized SWCNTs to deliver anti-sense oligos targeting lncRNAs in tumor. Due to their surface chemistry properties for delivery and large cargo capability, SWCNT represents a novel and useful nanomaterial for drug delivery, which not only stabilize nucleic acid molecule from digestion of nucleases, but increase penetration of DNA/RNA dramatically without toxicity. In our study, SWCNT was functionalized covalently and then conjugated with anti-MALAT1, which allow anti-MALAT1 to be released with high concentration in MM cells and induced DNA damage and apoptosis effectively in both in vitro and in vivo experiments without bringing any toxicity in normal cells. Thus SWCNT-anti-MALAT1 is an ideal therapeutic method for the MM patients.

Figure 8C:
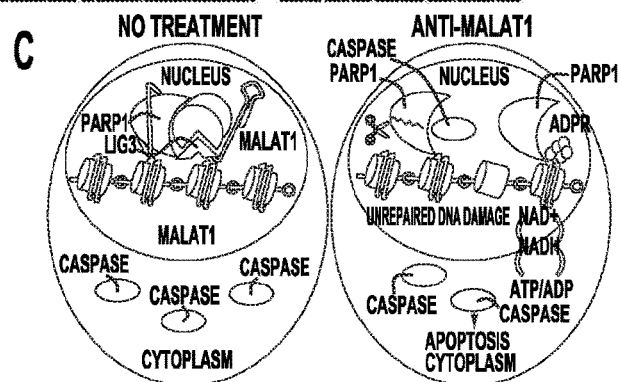

In conclusion, we have shown that MALAT1 exerted DNA protective and anti-apoptotic functions via binding to PARP1/LIG3 protein complexes, targeting MALAT1 induced DNA damage and apoptosis, therefore inhibited MM growth (FIG. 8C). Furthermore, we demonstrated that MALAT1 could be targeted via neutralization by antisense in vitro and in vivo, this treatment extended lifespan of MM-bearing mice significantly. Synergism of MALAT antisense with proteasome or PARP1 inhibitors further illustrated the potential therapeutic value of MALAT1 for MM patients.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating cancer in a subject in need thereof, comprising administering a therapeutically effective amount of an oligonucleotide having a size from 5 to 30 nucleotides that specifically hybridizes to human MALAT1 to the subject, wherein the cancer is drug resistant cancer selected from the group consisting of breast cancer, lung cancer, prostate cancer, hepatocellular carcinoma, and leukemia, or multiple myeloma, that has been demonstrated to exhibit MALAT1 overexpression, wherein the oligonucleotide is administered using a carbon nanotube.

2. The method of claim 1, wherein the cancer is multiple myeloma.

3. The method of claim 1, wherein the method further comprises administering a PARP1 and/or LIG3 inhibitor to the subject.

4. The method of claim 1, wherein the method further comprises administering a PARP1 inhibitor to the subject.

5. The method of claim 4, wherein the PARP1 inhibitor is selected from the group consisting of olaparib, rucaparib, BMN-673, niraparib, and iniparib.

6. The method of claim 1, wherein the method further comprises administering a LIG3 inhibitor to the subject.

7. The method of claim 6, wherein the LIG3 inhibitor is selected from the group consisting of L67 and L189.

8. The method of claim 1, wherein the subject is also undergoing one or more cancer therapies selected from the group consisting of surgery, chemotherapy, radiotherapy, thermotherapy, immunotherapy, hormone therapy, or laser therapy.

9. The method of claim 8, wherein the cancer therapy is bortezomib administration.

10. The method of claim 1, wherein the oligonucleotide is an antisense oligonucleotide.

11. The method of claim 1, wherein the oligonucleotide includes from 12 to 25 nucleotides.

12. The method of claim 1, wherein the oligonucleotide is a phosphorothioate-linked oligonucleotide.

13. The method of claim 1, wherein the oligonucleotide is a 2'-O-alkyl antisense oligonucleotide.

14. The method of claim 1, wherein the oligonucleotide consists of 25 or fewer nucleotides and comprises the nucleotide sequence SEQ ID NO: 1, SEQ ID NO: 2, or SEQ ID NO: 3.

* * * * *